(12) United States Patent
Miller

(10) Patent No.: US 11,612,414 B2
(45) Date of Patent: Mar. 28, 2023

(54) FIXATION CLAMP WITH SPACER

(71) Applicant: Austin Miller Trauma LLC, Germantown, TN (US)

(72) Inventor: Stephen T. Miller, Scotts Valley, CA (US)

(73) Assignee: Austin Miller Trauma LLC, Germantown, TN (US)

( * ) Notice: Subject to any disclaimer, the term of this patent is extended or adjusted under 35 U.S.C. 154(b) by 167 days.

(21) Appl. No.: 17/171,421

(22) Filed: Feb. 9, 2021

(65) Prior Publication Data

US 2021/0161560 A1 Jun. 3, 2021

Related U.S. Application Data

(62) Division of application No. 16/209,215, filed on Dec. 4, 2018, now Pat. No. 10,945,765.

(60) Provisional application No. 62/689,437, filed on Jun. 25, 2018, provisional application No. 62/595,344, filed on Dec. 6, 2017.

(51) Int. Cl.
*A61B 17/64* (2006.01)

(52) U.S. Cl.
CPC ........ *A61B 17/645* (2013.01); *A61B 17/6416* (2013.01); *A61B 17/6466* (2013.01); *A61B 2560/0406* (2013.01); *A61B 2560/0443* (2013.01)

(58) Field of Classification Search
CPC .............. A61B 17/6416; A61B 17/645; A61B 17/6466; A61B 17/6475
See application file for complete search history.

(56) References Cited

U.S. PATENT DOCUMENTS

| | | |
|---|---|---|
| 5,662,648 A | 9/1997 | Faccioli et al. |
| 5,800,548 A | 9/1998 | Martin et al. |
| 6,080,153 A | 6/2000 | Mata et al. |
| 6,409,729 B1 | 6/2002 | Martinelli et al. |
| 6,500,177 B1 | 12/2002 | Martinelli et al. |
| 7,004,943 B2 | 2/2006 | Ferrante et al. |
| 7,048,735 B2 | 5/2006 | Ferrante et al. |
| 7,241,074 B2 | 7/2007 | Thornke et al. |
| 7,320,556 B2 | 1/2008 | Vagn-Erik |
| 7,562,855 B2 | 7/2009 | Oetlinger |
| 7,708,736 B2 | 5/2010 | Mullaney |
| 7,887,537 B2 | 2/2011 | Ferrante et al. |

(Continued)

FOREIGN PATENT DOCUMENTS

CN 200354513 Y 12/1999

OTHER PUBLICATIONS

International Search Report and Written Opinion issued by the Korean InteliectuaL Property Office for International Patent Application No. PCT/US2018/064132 dated May 20, 2019.

*Primary Examiner* — Si Ming Ku
(74) *Attorney, Agent, or Firm* — KDB Firm PLLC

(57) ABSTRACT

A clamping device of an external fixation system that has a jaw set with a passage at one end configured to hold an element from a first range of sizes and a second passage configured to hold an element from a different range of sizes. The jaw set includes a first jaw, a second jaw, and a slider interposed between the first and second jaws that moves to a first position when the first element is located in the first passage and to a second position when the second element is located in the second passage.

18 Claims, 17 Drawing Sheets

(56) References Cited

U.S. PATENT DOCUMENTS

| | | |
|---|---|---|
| 7,938,829 B2 | 5/2011 | Mullaney |
| 8,241,285 B2 | 8/2012 | Mullaney |
| 8,734,446 B2 | 5/2014 | Miller |
| 8,821,491 B2 | 9/2014 | Chreene et al. |
| 8,827,997 B2 | 9/2014 | Cremer et al. |
| 9,138,260 B2 | 9/2015 | Miller et al. |
| 9,545,266 B2 | 1/2017 | Lessig et al. |
| 2002/0061225 A1 | 5/2002 | Boucher et al. |
| 2003/0149429 A1 | 8/2003 | Ferrante et al. |
| 2003/0233115 A1 | 12/2003 | Eversull et al. |
| 2006/0017566 A1 | 1/2006 | Gauvreau et al. |
| 2007/0049932 A1 | 3/2007 | Richelsoph et al. |
| 2007/0198012 A1 | 8/2007 | Thornke et al. |
| 2009/0036891 A1 | 2/2009 | Brown et al. |
| 2009/0088751 A1 | 4/2009 | Mullaney |
| 2009/0182278 A1 | 7/2009 | Eversull et al. |
| 2010/0030272 A1 | 2/2010 | Winslow et al. |
| 2011/0098706 A1 | 4/2011 | Mullaney |
| 2011/0098707 A1 | 4/2011 | Mullaney |
| 2011/0172663 A1 | 7/2011 | Mullaney |
| 2012/0004659 A1 | 1/2012 | Miller |
| 2012/0089142 A1 | 4/2012 | Mullaney |
| 2012/0095462 A1 | 4/2012 | Miller |
| 2012/0116262 A1 | 5/2012 | Houser et al. |
| 2012/0289959 A1 | 5/2012 | Miller |
| 2013/0281884 A1 | 10/2013 | Mullaney et al. |
| 2014/0214033 A1 | 7/2014 | Miller |
| 2014/0324045 A1 | 10/2014 | Cremer et al. |
| 2014/0364853 A1 | 12/2014 | Mullaney et al. |
| 2015/0305763 A1 | 10/2015 | Houser et al. |
| 2015/0351800 A1 | 12/2015 | Miller et al. |
| 2016/0175011 A1 | 6/2016 | Mullaney |
| 2017/0065300 A1 | 3/2017 | Mullaney et al. |
| 2017/0252069 A1* | 9/2017 | Muniz .............. A61B 17/6466 |
| 2018/0098793 A1 | 4/2018 | Miller et al. |
| 2018/0103987 A1 | 4/2018 | Mullaney et al. |

* cited by examiner

FIXATION CLAMP WITH SPACER

PRIORITY

This application is a divisional of pending U.S. application Ser. No. 16/209,215, filed Dec. 4, 2018, which application claims priority to and the benefit of the filing date of U.S. Provisional Patent Application 62/689,437, filed Jun. 25, 2018 and U.S. Provisional Patent Application 62/595,344, filed Dec. 6, 2017, both of which are incorporated by reference herein in their entireties.

BACKGROUND

External fixation systems are used to build frames that hold bone fixation elements, such as pins, bars, or rods, rigidly. The variability of the different conditions treated, such as bone fractures, requires versatility of alignment and sizing of the fixator frame. A very common style of external fixation system uses fixation elements, i.e. bars and bone pins, and clamps that hold the fixation elements together. Commonly, both pins and bars have circular cross sections, but typically, the bars are a larger diameter than the pins. For large frames for the leg and arm, the most common size bar is 11 mm, but they may vary between 8 and 13 mm, and the most common size pin is 5 mm, but they may vary between 3 and 6 mm. Clamps are used to join pins to bars and bars to other bars. The most common type of clamp has a threaded shaft that can squeeze together two jaw sets, clamping them together and clamping an element in each jaw set. Although a jaw set can be configured to grab a range of sizes of elements, fitting elements that have an over two times difference in diameter in a jaw set that is both compact in size and effective in locking strength has been a challenge. For this reason, most clamp systems have jaws configured to either grab a bar or a pin, and therefore have a clamp that is configured to grab a bar in one jaw set and a pin in another jaw set and another separate clamp assembly that is configured to grab a bar in each jaw set.

Having separate clamps for joining two bars versus joining a bar to a pin can lead to problems. The user can accidentally get handed the wrong one during a medical procedure, leading to wasted time. The shaft tightening element can be in an inconvenient location for the desired frame geometry. Also, the number of clamps needing to be sterilized and made available for each case is increased. To overcome some of these shortcomings, clamps that can accept bars and pins in each jaw set have been developed. One of the earliest is the Synthes combination clamp that has two grooves on each jaw in the jaw set, one groove sized for bars and one sized for pins. These jaws accept the bar or pin element by spreading apart to allow the element into the groove, and they grip the element by being squeezed together via the shaft onto the element.

FIGS. 1a and 1b show such a conventional clamp 10. This clamp has a first jaw set 11 and a second similar jaw set 11a. The two jaw sets are similar, so the similar items in the second jaw set are numbered the same as the first jaw set but have an "a" appended. Each jaw set is configured to hold either of a first fixation element 12 or a second fixation element 13. In some examples, the first jaw set includes an outer jaw 15 and an inner jaw 16. The outer jaw 15 has a first groove 17 and a second groove 18. The inner jaw 16 has a first groove 19 and a second groove 20. The first grooves 17 and 19 form a first passage 21, and the second grooves 18 and 20 form a second passage 22. The first element 12 can be placed in the first passage 21 and the inner jaw 16 and outer jaw 15 open slightly, contacting near the second passage 22 at an edge 23. As shown in FIG. 1a, in the second jaw set 11a, a second element 13 may be placed in the second passage 22a. The inner jaw 16a and outer jaw 15a open slightly, contacting near the first passage 21a at edge 24. As shown in FIG. 1b, when a third element 14 of a similar size to the first element 12 is placed in the first passage 21a, the second jaw set 11a may contact on the edge 23a. In various embodiments, to clamp the elements into the jaw sets, a threaded shaft 25 and nut 26 may be tightened compressing both jaw sets and the elements. Because the edges in contact 23 and 24 are closer to the force of clamping than the elements 12, 13, or 14, the edges may carry a greater share of the clamping load. Also, because both the first passage 21 and second passage 22 are accessible to the user, an element might mistakenly be introduced into a jaw set when another element is already in place, forcing the two elements to be parallel. Although there may be an instance where this is desired, most often the goal is to get the elements clamped together in a non-parallel orientation.

Another concept by Chreene and Austin (U.S. Pat. No. 8,821,491) is similar, but the jaws in each set slide laterally relative to each other to allow the bar or pin element to enter the jaw. The Chreene clamp grips the element by being squeezed onto the element as well.

Both the Synthes combination clamp and the Chreene design have drawbacks. One example drawback is that the amount of force transferred to the element by the jaw geometry is reduced relative to a standard one sided clamp. In these two-jaw style clamp designs, the locking force generated by the shaft is split between the clamping of the element and the reaction force between the two jaws where they pivot. Because the location of contact between the two jaws is moved closer to the line of action of the clamping force, the relative reaction force at this location goes up, and the reaction force acting between the jaw and the element goes down.

Another jaw set that can hold more than one size of element is shown in Cremer et al (U.S. Pat. No. 8,827,997). The jaw set used to clamp the element has three, and only three, sets of passages. Each set of passages is designed to hold an element of a particular size. It has similar drawbacks to the two-sided designs discussed above.

Another method used to clamp elements of vastly different sizes is shown by Brown and Denlinger (US Patent Publication 2009/0036891). The jaw set has two passages located on one side of the clamping fastener, a smaller passage close to the fastener and a larger passage further from the fastener.

Another method to clamp elements of varying sizes is shown by Miller and Mullaney (U.S. Pat. No. 9,138,260), where the jaw set has a passage or other clamping means on one side of the fastener. On the other side of the fastener, a spacer that has steps or catches is interposed between the jaws. Depending upon where the spacer is positioned, the jaw is arranged to hold an element of a specific size by allowing the jaws to move to a position where the passage is allowed to open to a particular size. The primary purpose of the spacer in this design is to configure the clamp to provisionally lock the element when the spacer is in the correct position. One drawback of this design is the spacer can move to the wrong position such that the jaw set is configured for a different element size than intended. Another drawback is that it is difficult to configure the jaw passage and the steps such that elements of as much as two times difference in size can be effectively gripped.

Accordingly, there is a need for additional external fixation clamps that may address at least one of the deficiencies in the state of the art, whether stated above or unstated.

BRIEF SUMMARY OF THE INVENTION

Consistent with some embodiments, the basic design of an external fixation system clamp incorporates a jaw set that grips the fixation element and a fastener that squeezes the jaw set together. Most clamps have two jaw sets so that two fixation elements can be clamped together, but a single jaw set may be attached to another device to clamp a fixation element to that other device. Each jaw set is made up of two jaw halves. Usually, the jaw halves are separate components that rest against each other, with a first end of each component forming a passage for accepting the fixation element and a second end of the component balancing the clamping load. The fastener that applies the clamping load may be interposed between the passage and the back end of the jaw component.

A first benefit of the systems described herein is the ability to clamp differently sized or shaped elements in a single jaw set. Most external fixation systems have a variety of differently sized elements. The most common pattern is a larger bar for spanning across the defect and a smaller pin for fixing into the bone. By having a jaw set that can grab either the bar or the pin, or any of two fixation elements, the jaw set can be used in a variety of situations. This reduces the need for a number of different clamps with different jaw sets specific to each fixation element.

A second benefit of systems described herein is that they may provide a higher clamping load onto the fixation element for the same fastener load. Other devices which allow for a jaw set to grip more than one size fastener have a compromise in their geometry that reduces the amount of fastener load transferred through the fixation element due to the balance of forces on the jaws. By utilizing the slider to position the reaction force further from the fastener load, the grip force utilizes a higher amount of the fastener load. This benefits the user because they can get better stability when pre-tightening the clamp using just finger force. Finger force may be sufficient to keep the clamp from slipping on them prior to final tightening. Further, final tightening will be more stable for the same amount of load applied to the fastener.

An example embodiment described herein comprises jaw components, each with a groove on a first end together forming a passage for a larger fixation element and grooves on the opposite second end together forming a passage for a smaller fixation element. Positioned between these two jaw components is a slider. When a fixation element is introduced into the desired passage, the slider is moved towards the unused passage. The slider is positioned so the clamping force is transmitted from one jaw component to the other through the fixation element and the slider. The slider is configured so that the contact point between the outer jaw and slider and between the slider and inner jaw is located in a position away from the fastener opposite the fixation element.

The fastener applies load to the outer jaw, which shares this load between the element and the slider. The further the contact point with the slider is moved away from the fastener, the higher the amount of load sharing that is sent through the element. Conventional combination clamps which do not have a slider have a contact point that is very close to the fastener, which means that a high share of the load goes through the contact point and a low share goes through the element.

An example embodiment comprises a slider interposed between two jaws that tip up and down relative to each other to allow the fixation element into the passage. Another configuration positions a slider between an inner jaw and an outer jaw, where the outer jaw slides relative to the inner jaw to allow the fixation element into the passage. To apply load to the fastener in either passage, the fastener must be slightly larger than the passage. For the conventional sliding head clamp, the outer jaw must tip relative to the inner jaw to allow the outer jaw to slide back in place. Although this tipping will be small, in practice, the fastener loads the outer jaw unevenly. In one embodiment of the invention, the outer jaw and slider are configured to contact only at the point furthest from the retained fastener. The outer jaw has a relief in the track where it contacts the slider. When the fixation element is in place, the slider is moved to a point where the near side is located adjacent to the relief and the far side is in contact with the outer jaw.

The jaw set can be connected to a matching jaw set. The example embodiment shows radial serrations on the inside of the inner jaw that can interface with matching serrations on a matching inner jaw of the matching jaw set. These same serrations can mate with matching serrations on other devices as well. When the fastener is tightened, the serrations lock together while the fixation element is clamped.

The jaw set can be mated to other jaw sets or other devices through other means. One embodiment attaches the jaw set to a ball joint, so the jaw set can swivel relative to the other device. Another embodiment has the inner jaw mated to a saddle so the jaw set can roll relative to the other device.

In yet another exemplary aspect, the device may be an external fixation frame that includes a clamp with a jaw set where one side is configured to hold a first element and the other side of the jaw set is configured to hold a second, differently shaped or sized element, where a slider is interposed between the first jaw of the jaw set and the second jaw of the jaw set, and where the slider slides between a first position and a second position where the first position aids in holding the first element and the second position aids in holding the second element.

In an exemplary aspect, the present disclosure is directed to an external fixation clamp configured to hold a fixation element. The external fixation clamp may include an inner jaw with a first end shaped to engage a first size fixation element and a second end shaped to engage a second size fixation element. An outer jaw may include a first end shaped to engage the first size fixation element and a second end shaped to engage the second size fixation element. A fastener may be configured to clamp the inner jaw and the outer jaw to at least one of the first and the second fixation elements, and the fastener may have an axis. A sliding spacer may be interposed between the inner jaw and the outer jaw and may be arranged to slide in a direction transverse to the axis of the fastener. The sliding spacer may be structurally associated with the inner jaw and the outer jaw so that when the first size fixation element is introduced between the inner jaw and the outer jaw, the sliding spacer moves to a first position where the sliding spacer and at least one of the inner jaw and the outer jaw are in contact at a first point away from the fastener. When the second size fixation element is introduced between the inner jaw and the outer jaw, the sliding spacer may move to a second position where the sliding spacer and at least one of the inner jaw and the outer jaw are in contact at a second point away from the fastener.

In some aspects, the outer jaw is configured to tilt relative to the inner jaw to allow the fixation element to enter between the inner jaw and the outer jaw. In some aspects, the outer jaw slides relative to the inner jaw to allow the fixation element to enter between the inner jaw and the outer jaw. In some aspects, the first ends of the inner jaw and the outer jaw are configured to hold a fixation element of a diameter between 10 and 13 mm, and the second ends of the inner jaw and the outer jaw are configured to hold a fixation element of a diameter between 3 and 6.5 mm. In some aspects, the first ends of the inner jaw and the outer jaw are configured to hold a fixation element of a diameter between 6 and 9 mm, and the second ends of the inner jaw and the outer jaw are configured to hold a fixation element of a diameter between 3 and 5 mm. In some aspects, the first ends of the inner jaw and the outer jaw are configured to hold a fixation element of a diameter between 4 and 6 mm, and the second ends of the inner jaw and the outer jaw are configured to hold a fixation element of a diameter between 2 and 4 mm. In some aspects, the first ends of the inner jaw and the outer jaw are configured to hold a fixation element of a diameter of 11 mm, and the second ends of the inner jaw and the outer jaw are configured to hold a fixation element of a diameter of 5 mm. In some aspects, the clamp further includes a second inner jaw disposed along the axis relative to the first inner jaw; and a second outer jaw, wherein the second inner and second outer jaws are disposed to cooperatively grip a second fixation element. In some aspects, the clamp may include a saddle component, and the inner jaw may be configured to mate with the saddle component in a manner that allows the inner jaw, the outer jaw, and the sliding spacer to roll about an angle transverse to an axis of one of the first size fixation element and the second size fixation element and also transverse to the axis of the fastener. In some aspects, the inner jaw is configured to mate with a ball such that the inner jaw and the outer jaw is configured to pitch, roll, and yaw relative to a device comprising the ball.

In another exemplary aspect, the present disclosure is directed to a jaw set of an external fixation clamp. The jaw set may include an inner jaw with a first end configured to engage a first fixation element and a second end configured to engage a second fixation element, an outer jaw with a first end configured to engage the first fixation element and a second end configured to engage the second fixation element, and a fastener configured to clamp the inner jaw and the outer jaw to one of the first fixation element and the second fixation element. The fastener may have an axis. A sliding spacer may cooperatively engage the inner jaw and the outer jaw and may slide in a direction transverse to the axis of the fastener and transverse to an axis of said one of the first fixation element and the second fixation element when said one of the first fixation element and the second fixation element is disposed between the inner jaw and the outer jaw. When said one of the first fixation element and the second fixation element is introduced between the first end of the inner jaw and the first end of the outer jaw, the sliding spacer may move to a first position where the sliding spacer and at least one of the inner jaw and the outer jaw are in contact at a first location near the second end of the inner jaw or the outer jaw. Alternatively, when said one of the first fixation element and the second fixation element is introduced between the second end of the inner jaw and the outer jaw, the sliding spacer may move to a second position such that the sliding spacer and at least one of the inner jaw and the outer jaw are in contact at a second location near the first end of the inner jaw or the outer jaw.

In an aspect, the first end of the inner jaw and the first end of the outer jaw form a first passage configured to hold the first fixation element of a first size and the second end of the inner jaw and the second end of the outer jaw form a second passage configured to hold the second fixation element of a second size different than the first size. In an aspect, the first end of the inner jaw and the first end of the outer jaw form a first passage configured to hold the first fixation element when the first fixation element is a non-cylindrical element and the second end of the inner jaw and the second end of the outer jaw form a second passage configured to hold the second fixation element when the second fixation element is a different shape than the non-cylindrical element. In an aspect, the second end of the inner jaw and the second end of the outer jaw form are configured to hold the second fixation element when the second fixation element is a cylindrical element. In an aspect, the second end of the inner jaw and the second end of the outer jaw form are configured to hold the second fixation element when the second fixation element is proportionally the same shape as the first fixation element but a different size from the first fixation element.

In another exemplary aspect, the present disclosure is directed to an external fixation clamp configured to grip a size-range of fixation elements. The clamp may include an inner jaw with a first end and a second end, and may also include an outer jaw with a first end and a second end. The first end of the inner jaw and the first end of the outer jaw may be disposed to cooperatively form a first passage sized to grip a first fixation element having a first size. The second end of the inner jaw and the second end of the outer jaw may be disposed to cooperatively form a second passage sized to grip a second fixation element having a second size. A fastener may be configured to clamp the inner jaw and the outer jaw to at least one of the first and the second fixation elements. The fastener may have a fastener axis. A spacer may be slidingly moveable relative to the inner jaw and the outer jaw. The spacer may be arranged to slide and intersect the second passage when the first fixation element having a first size is introduced to the first passage. The spacer may be arranged to slide and intersect the first passage when the second fixation element having a second size is introduced to the second passage.

In another exemplary aspect, the present disclosure is directed to an external fixation clamp configured to grip a size-range of fixation elements. The clamp may include the inner jaw, the outer jaw, the fastener, and the spacer. The spacer may be slidingly moveable relative to the inner jaw and the outer jaw and slidable between the first and the second passages. The spacer may engage one of the inner jaw and the outer jaw at a first fulcrum point when the first fixation element having a first size is introduced to the first passage. The spacer may engage one of the inner jaw and the outer jaw at a second fulcrum point when the second fixation element having a second size is introduced to the second passage. The first fulcrum point may be disposed on a first lateral side of the fastener axis and the second fulcrum point may be disposed on a second different lateral side of the fastener axis.

In another exemplary aspect, the present disclosure is directed to an external fixation clamp jaw set having an outer jaw, an inner jaw, and a fastener. The claim may also have a swivel component with a convex surface shaped to mate to the concave surface of the inner jaw. The inner jaw may be configured to mate with the swivel component and allow the inner jaw and the outer jaw to roll about an axis transverse to both the axis of the fixation element and the axis of the fastener.

In an aspect, the second end of the inner jaw and the second end of the outer jaw are disposed to cooperatively form a second passage sized to grip a second fixation element having a second size. The clamp jaw set may further include a sliding spacer slidably associated with the inner jaw and the outer jaw to slide in a direction transverse to the axis of the fastener. The spacer may be structurally associated with the inner jaw and the outer jaw so that when the first size fixation element is introduced into the first passage, the sliding spacer moves to a first position where the sliding spacer and at least one of the inner and the outer jaws are in contact at a first location away from the fastener. Alternately, when the second size fixation element is introduced into the second passage, the sliding spacer may move to a second position where the sliding spacer and at least one of the inner and the outer jaws are in contact at a second location away from the fastener.

In an aspect, the swivel component is configured to lock the first and the second jaws at a tilt relative to the fastener at the same time the fastener clamps the inner jaw and the outer jaw to at least one fixation element. In an aspect, the convex surface of the swivel component is a toroidal shape. In an aspect, the convex surface of the swivel component is a cylindrical shape. In an aspect, the convex surface of the swivel component is a shape consisting of two cones. In an aspect, the convex surface of the swivel component is a partial sphere. In an aspect, the swivel component has a serrated surface opposite the convex surface. In an aspect, the outer jaw has a convex surface. In an aspect, the convex surface of the outer jaw mates with a flat surface of the fastener. In an aspect, the convex surface of the outer jaw mates with a washer interposed between the outer jaw and the fastener. In an aspect, the washer incorporates a convex surface to contact the outer jaw.

In an aspect, the present disclosure is directed to an external fixation clamp that includes a jaw set including an outer jaw and an inner jaw forming a passage therebetween. The jaw set may be configured to capture a rigid fixation element within the passage. The inner jaw may have a concave cavity on the surface facing away from the outer jaw. A clamping mechanism may be arranged to maintain an axial alignment of the outer jaw and the inner jaw. A reference component may be offset along the longitudinal axis from the jaw pair. A coupling mechanism may be arranged between the jaw set and the reference component. The coupling mechanism may allow the jaw set to rotate relative to the reference component about the longitudinal axis. The coupling mechanism may include a convex surface interfacing with the concave cavity on the surface of the inner jaw facing away from the outer jaw, and the jaw set may be pivotable on the coupling mechanism about a transverse axis that is perpendicular to the longitudinal axis.

In an aspect, the clamping mechanism is a nut combined with a threaded stud. In an aspect, the nut comprises a flat surface that articulates against a curved outer surface of the outer jaw, and the nut may be rotatable to lock articulation of the jaw set when tightened on the stud. In an aspect, the clamp may include a washer between the nut and the curved outer surface of the outer jaw. In an aspect, the washer comprises a curved surface that fits against the curved outer surface of the outer jaw. In an aspect, the jaw set is configured to capture a rigid element of a second size.

In an aspect, reference component consists of an external fixation clamp configured to hold a fixation element. The reference component may include an inner jaw with a first end shaped to engage a first size fixation element and a second end shaped to engage a second size fixation element. An outer jaw with a first end may be shaped to engage the first size fixation element and a second end shaped to engage the second size fixation element. A fastener may be configured to clamp the jaws to at least one of the first and the second fixation elements, the fastener having an axis. A sliding spacer may be interposed between the jaws arranged to slide in a direction transverse to the axis of the fastener. In an aspect, the clamping mechanism locks both fixation elements and the articulation device when applying clamping force.

BRIEF DESCRIPTION OF THE DRAWINGS

The accompanying drawings illustrate embodiments of the devices and methods disclosed herein and together with the description, serve to explain the principles of the present disclosure.

DETAILED DESCRIPTION

Figure 1A:
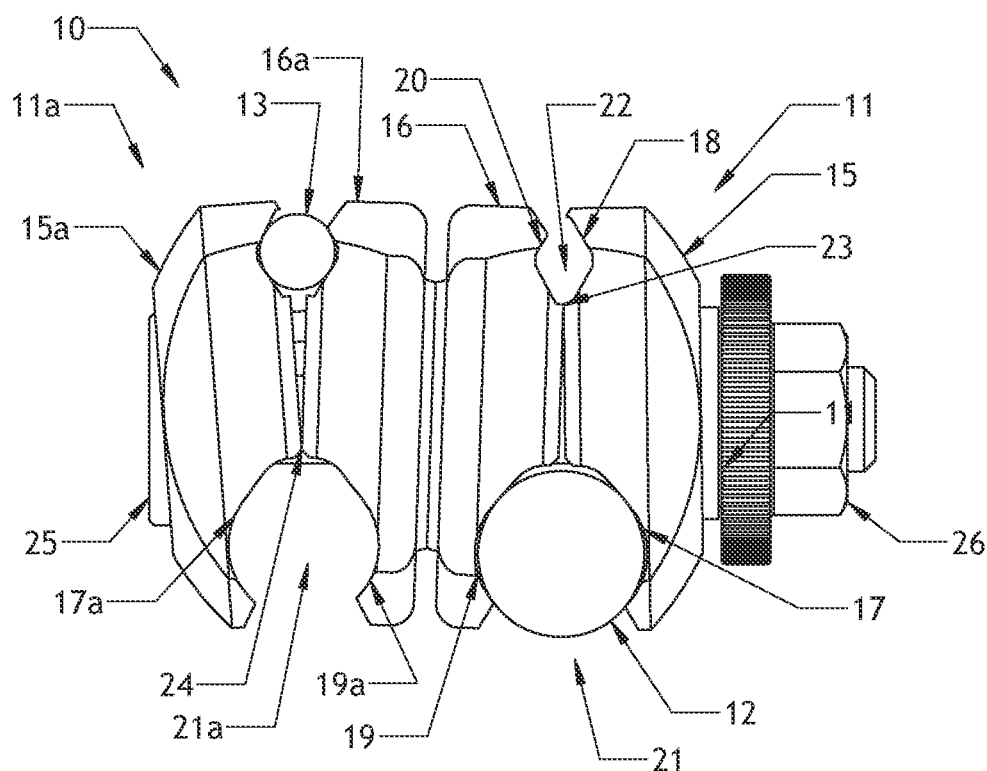
FIG. 1a shows a conventional device with jaw sets that have two passages where the first passage is configured to hold an element of a first size and the second passage is configured to hold an element of a different size.

For the purposes of promoting an understanding of the principles of the present disclosure, reference will now be made to the embodiments illustrated in the drawings, and specific language will be used to describe the same. It will nevertheless be understood that no limitation of the scope of the disclosure is intended. Any alterations and further modifications to the described devices, instruments, methods, and any further application of the principles of the present disclosure are fully contemplated as would normally occur to one skilled in the art to which the disclosure relates. In particular, it is fully contemplated that the features, components, and/or steps described with respect to one embodiment may be combined with the features, components, and/or steps described with respect to other embodiments of the present disclosure.

Figure 2:
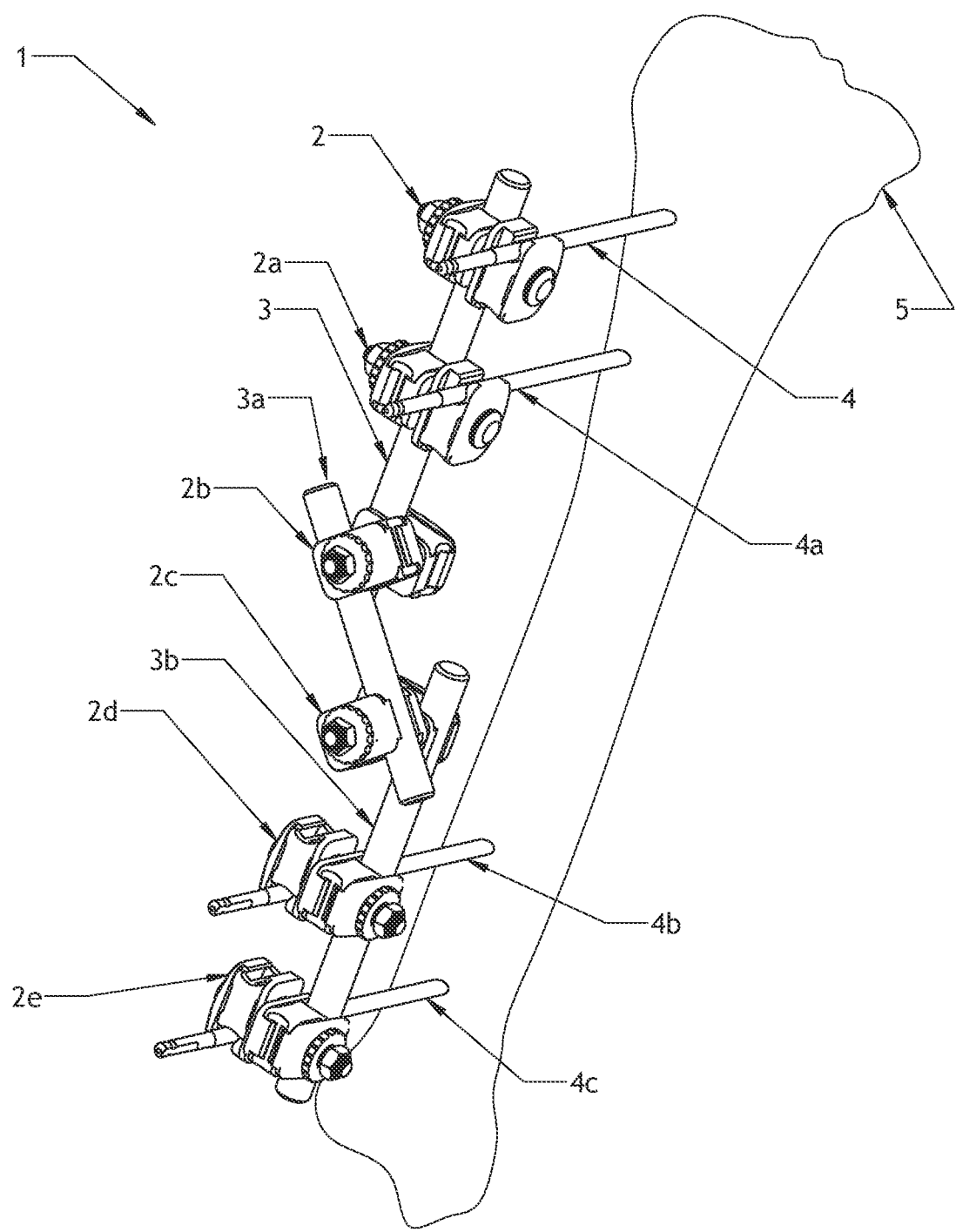
FIG. 2 shows one type of simple external fixation frame that uses clamps which incorporate the jaw sets of the present invention according to one or more aspects of the present disclosure.

FIG. 2 shows one type of external fixation frame 1. The frame may be held together with a number of clamps 2, 2a, 2b, 2c, 2d, 2e. Each clamp may hold two fixation elements together. In an exemplary embodiment, they hold bars 3, 3a, 3b and bone pins 4, 4a, 4b, 4c. The bone pins are fixed into the bone 5. The rods and bone pins are significantly different sizes. Here, the different sizes are represented by cross-section widths, which may be diameters. The sizes may vary and, in some implementations, the sizes of the bars may be double or more than double the sizes of the pins. In some implementations however, the sizes of the bars may be less than double the size of the pins. The clamps, in this depiction, are all the same style and design. The clamps incorporate jaw sets of the present invention such that the clamps can effectively clamp a bar to another bar or can clamp a bar to a pin. Different configurations of clamp 2 are discussed below, and other types of clamps are contemplated.

Figure 3:
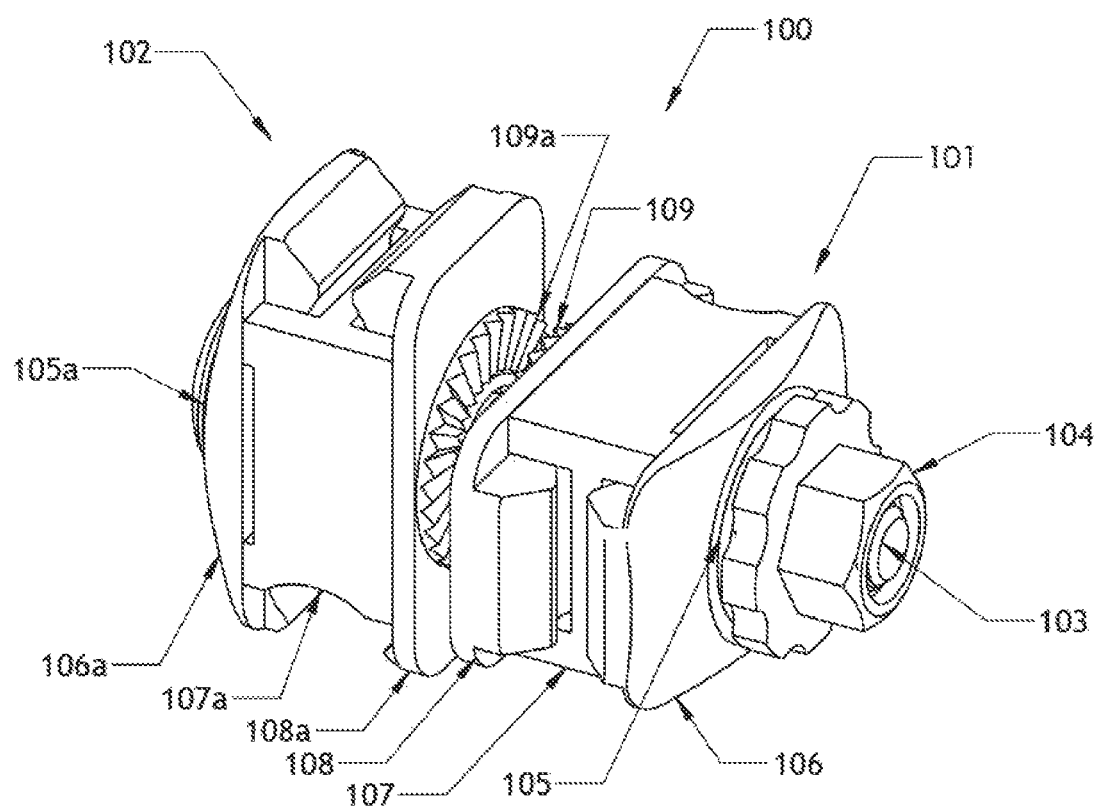
FIG. 3 is a perspective view of a clamp according to one or more aspects of the present disclosure.

FIG. 3 is a perspective view of an external fixation clamp assembly 100 made with the example embodiment jaw set 101 according to one or more aspects of the present disclosure. The jaw set 101 includes an outer jaw 106, a spacer 107, and an inner jaw 108. Here, this clamp assembly 100 may incorporate a second similar jaw set 102, but depending on the implementation and the embodiment, other jaw sets or other external fixation devices could be mated to the first jaw set in place of or in addition to the jaw set 102. To apply clamping force to the jaw set 101, a threaded shaft 103 (also referred to herein as a fastener) and nut 104 act on the other jaw set 102 and a washer 105. The washer 105 may be seated on the outside of the outer jaw 106 of the jaw set 101. In some examples, the outer jaw 106 may rest against the spacer 107 which may rest against the inner jaw 108. In this example implementation, the second jaw set 102 in FIG. 3 includes a similar washer 105a, outer jaw 106a, spacer 107a, and inner jaw 108a. In some embodiments and as shown in FIG. 3, the inner jaw 108, 108a may have rotation resisting serrations 109 which seat into similar serrations 109a on the opposing component, which in this example is the inner jaw 108a of the jaw set 102. Other rotation resisting features are contemplated, which may include relying solely on the force of friction. The threaded shaft or fastener may define an axis that is coaxial with the threaded shaft, which may also define an axis of the fixation clamp assembly 100.

In some implementations described in FIG. 3 and in other embodiments throughout this disclosure, the threaded shaft 103 (or fastener) and the nut 104 may form a clamping mechanism arranged to maintain an axial alignment of the outer jaw and the inner jaw.

Furthermore, although FIG. 3 shows the first jaw set 101 and the second jaw set 102, the second jaw set 102 may also be referred to as a reference component. Although shown as a jaw set, the reference component may be a different component, such as a stabilizer, a multi-pin clamp, or other component that may be used as a reference when the first jaw set 101 is rotated, pivoted, or otherwise displaced to manipulate a fixation element.

Figure 4:
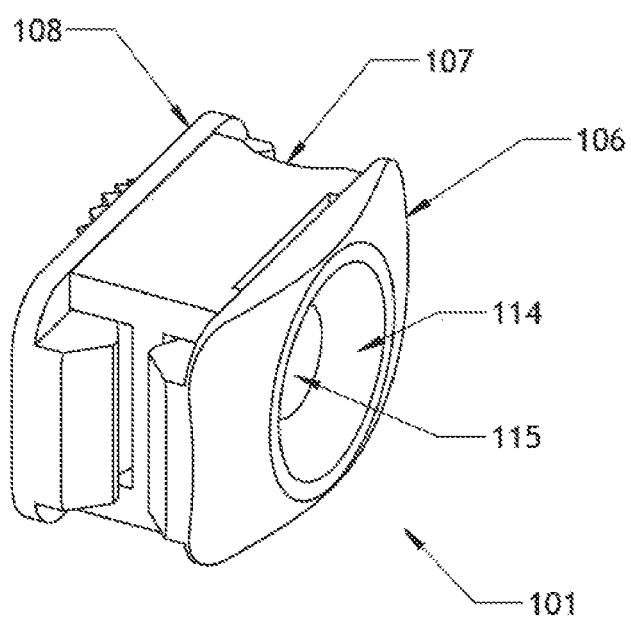
FIG. 4 is a perspective view of a jaw set of FIG. 3 according to one or more aspects of the present disclosure.

FIG. 4 shows the jaw set 101 in a perspective view according to one or more aspects of the present disclosure. The outer jaw 106 of the jaw set 101 may incorporate a seat 114 for the washer and a bore 115 through which the shaft 103 may pass through. Depending on the embodiment, the seat may be a tapered at an angle, may be bowl-shaped, or may have some other shape.

Figure 5:
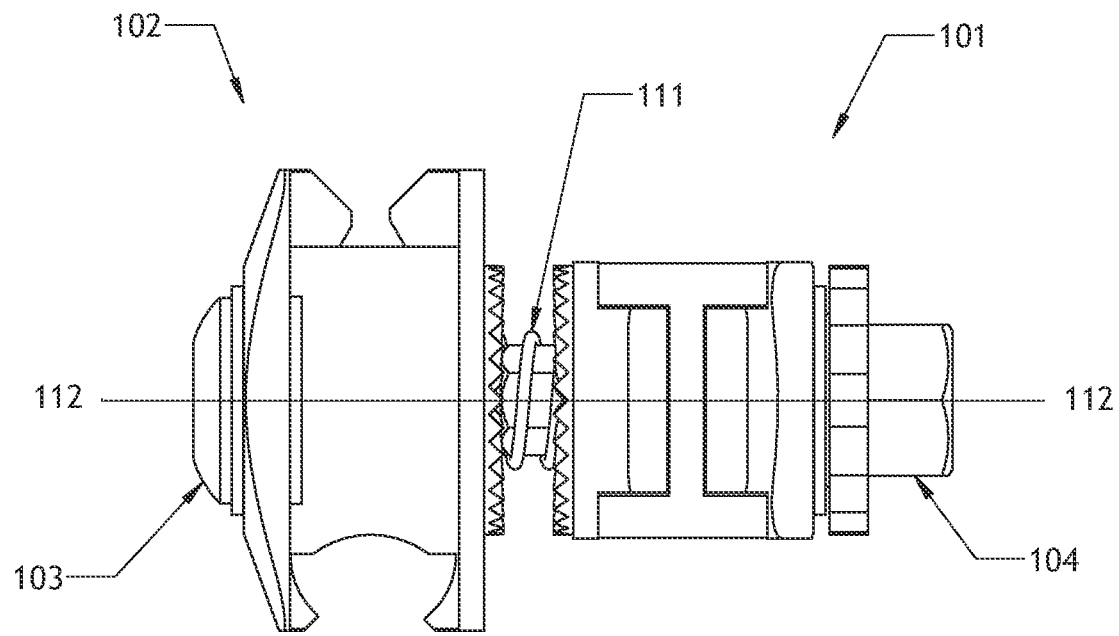
FIG. 5 shows a plan view of the clamp of FIG. 3 according to one or more aspects of the present disclosure.

FIG. 5 shows the clamp from FIG. 3 from a side view according to one or more aspects of the present disclosure. Visible in this view is a spring 111, which in some embodiments may bias and selectively hold the jaw sets apart. The spring is a biasing feature that may make the clamp easier to snap onto the fixation element and remain in place prior to tightening, but the spring may not be required for the device to function. Tightening the nut 104 compresses the jaw sets 101, 102 against the head of the shaft 103. A line 112-112 is drawn to show substantially the center of the shaft.

Figure 6:
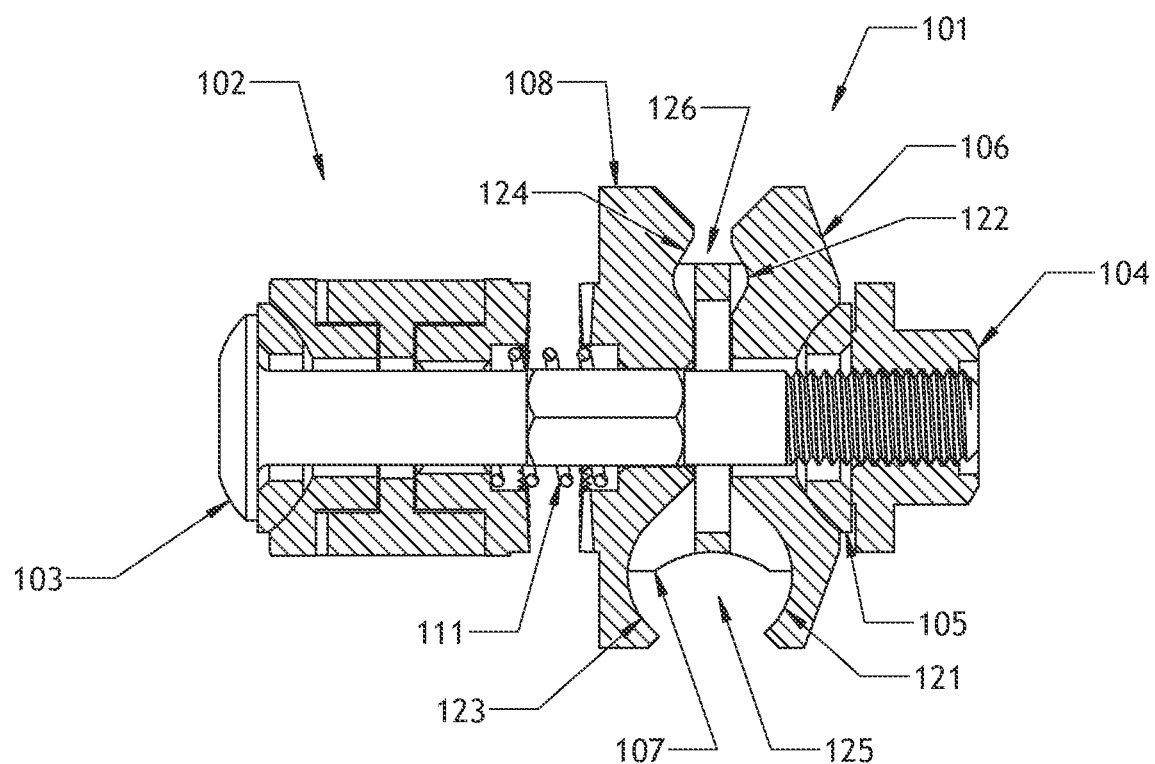
FIG. 6 shows a partial section view of the clamp taken through line 112-112 in FIG. 5 according to one or more aspects of the present disclosure.

FIG. 6 is a section view taken through FIG. 5 along line 112-112 according to one or more aspects of the present disclosure. In some embodiments, the section view shows that the outer jaw 106 may have a first groove 121 and a second groove 122. The first and second grooves 121, 122 are the same size in FIG. 6, but they may have different sizes, including having a groove on only one of the jaws. They are shown as exactly opposing each other in this implementation, but may be partially offset in other implementations. Similarly, the inner jaw 108 may have a third groove 123 and a fourth groove 124. When the jaw set 101 is assembled, the first and third groove 121, 123 may combine to form a first passage 125 to grip a fixation element, and the second and fourth groove 122, 124 may combine to form a second passage 126 to grip a differently sized fixation element.

Figure 7A:
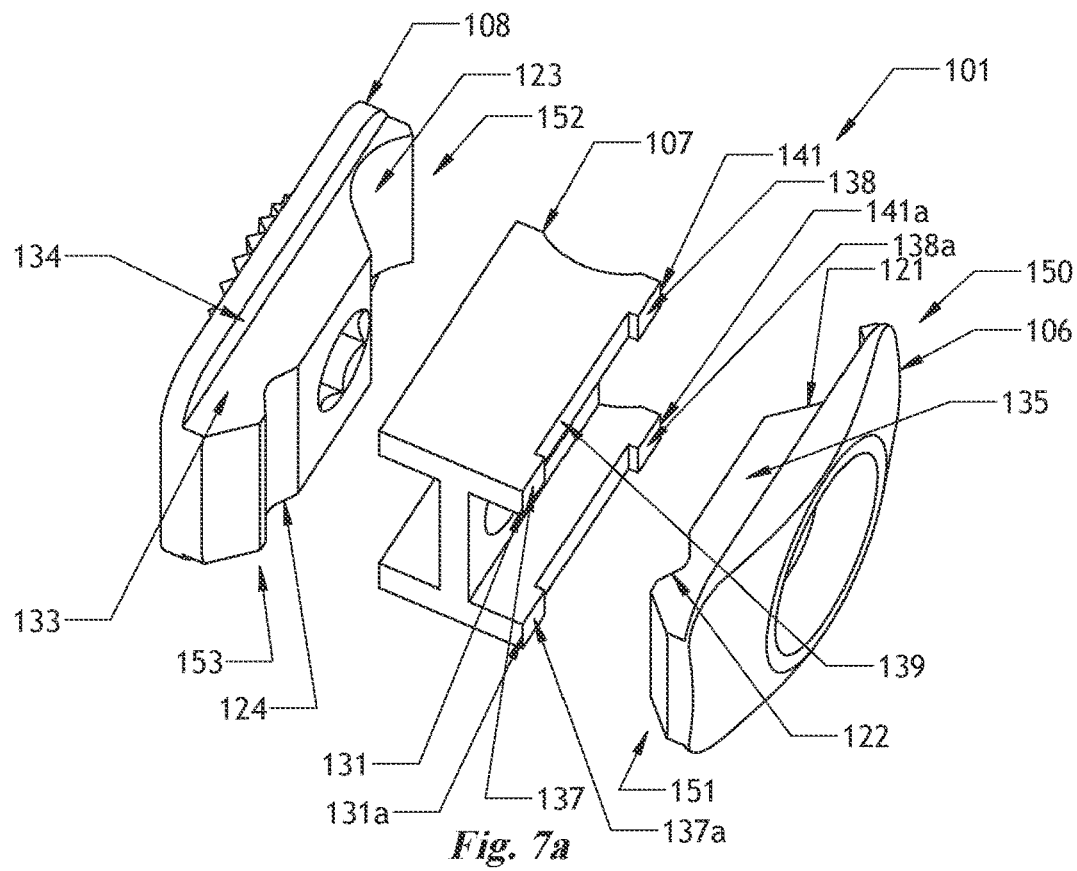
FIG. 7a shows an exploded view of the jaw set according to one or more aspects of the present disclosure.
Figure 7B:
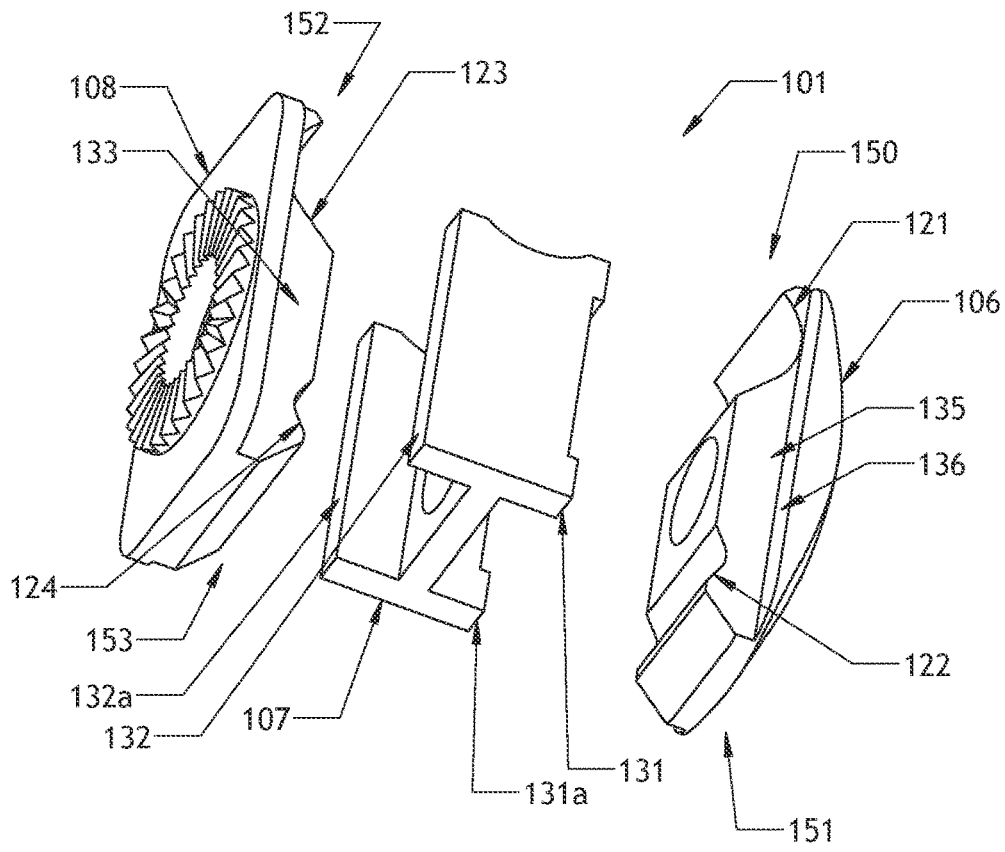
FIG. 7b shows another exploded view of the jaw set according to one or more aspects of the present disclosure.

FIGS. 7a and 7b show an exploded view of the jaw set 101 from two different perspectives according to one or more aspects of the present disclosure. In some embodiments, the inner jaw 108 shows a track 133 with a bearing surface 134. The spacer 107 may have a bearing surface 132 that contacts the inner jaw 106 on the mating bearing surface 134. The spacer may also have bearing surfaces 137 and 138 on its opposite side. In some embodiments, the outer jaw 106 shows a track 135 with a bearing surface 136. The outer jaw bearing surface 136 may contact the spacer bearing surface 137 and 138. In an exemplary embodiment, since each of the outer jaw 106, the spacer 107, and the inner jaw 108 is symmetrical, each has additional symmetrically matching bearing surfaces 132a, 137a, 138a, and not shown, 134a, 136a. In various embodiments, on the spacer 107, between bearing surfaces 137 and 138, there is a relief 139 shown in FIG. 7a. In an exemplary embodiment, bearing surfaces 137 and 138 are coplanar surfaces, but other arrangements are contemplated. Edge 131 is shown at the outer edge of bearing surface 137. Edge 141 may be located on the other side of the spacer 107 at the outer edge of bearing surface 138. Similar edges 131a and 141a may be located at the outer edges of surfaces 137a and 138a.

The outer jaw 106 and the inner jaw 108 each include two element-receiving ends, that in this implementation are opposed to each other. Here, the outer jaw 106 includes a first element-receiving end 150 and a second element-receiving end 151. The inner jaw 108 also includes a first element-receiving end 152 and a second element-receiving end 153. Each of the element-receiving ends 150, 151, 152, 153 are shaped to engage a fixation element, such as a bar or a pin introduced into the jaw set formed by the outer jaw and the inner jaw. In the embodiment shown, first element-receiving ends 150, 152 of the outer and inner jaws 106, 108 are shaped to engage a first size fixation element and the second element-receiving ends 150, 152 of the outer and inner jaws 106, 108 are shaped to engage a second size fixation element. In the implementation shown, the first element receiving end 150 of the outer jaw 106 and the first element receiving end 152 of the inner jaw 108 cooperate to define the passage 125. Likewise, the second element receiving end 151 of the outer jaw 106 and the second element receiving end 154 of the inner jaw 108 cooperate to define the passage 126.

Figure 8:
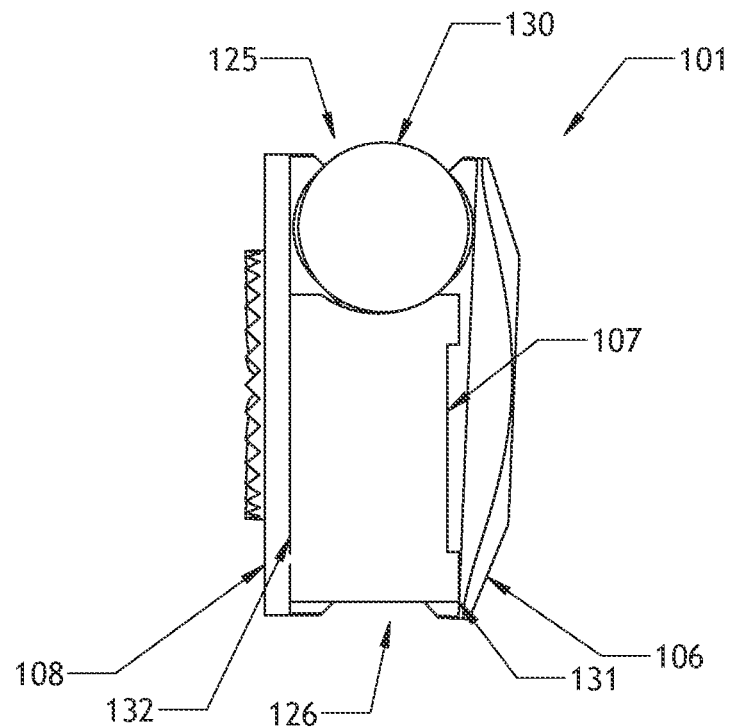
FIG. 8 shows the jaw set holding an element of a first size in the first passage according to one or more aspects of the present disclosure.

FIG. 8 shows the jaw set 101 in a first position where the sliding spacer 107 and at least one of the inner and outer jaws 108, 106 are in contact at a first point away from the fixation element and away from the fastener or threaded shaft 103. Here, a fixation element 130 may be located in the first passage 125 of the jaw set 101. In this embodiment, the element 130 may be a fixation bar, having a size or diameter greater than a size or diameter of a fixation pin. In an exemplary embodiment, the spacer 107 is moved away from the first passage 125, and the outer jaw 106 is in contact with the spacer 107 at contact points that correspond to the reference number 131 in FIG. 8 on the outer edges 131, 131a of the spacer 107 furthest from the element. The contact point that corresponds to the reference numbers 131 in FIG. 8 may act as a fulcrum for the outer jaw to pivot or rotate to increase or decrease the width of the passage 125. Although shown as a contact point with the outer jaw 106, other embodiments utilize a contact point or contact fulcrum with the inner jaw, while yet other embodiments utilize contact points or contact fulcrums on both the inner and outer jaws 108, 106 at the same time. Because the spacer may be displaced away from the element 130, the edges in contact may be located away from the shaft 103. In the configuration shown in FIG. 8, the spacer 107 is also preventing introduction of an element into the second passage 126. It may do this because the sliding spacer 107 intersects with the first passage 126 and mechanically interferes or blocks introduction of an element into the second passage. It is worth noting that some implementations of the spacer 107 includes a depression or recess portion that may engage or abut against the outer surface shape of the fixation element 130.

Figure 9:
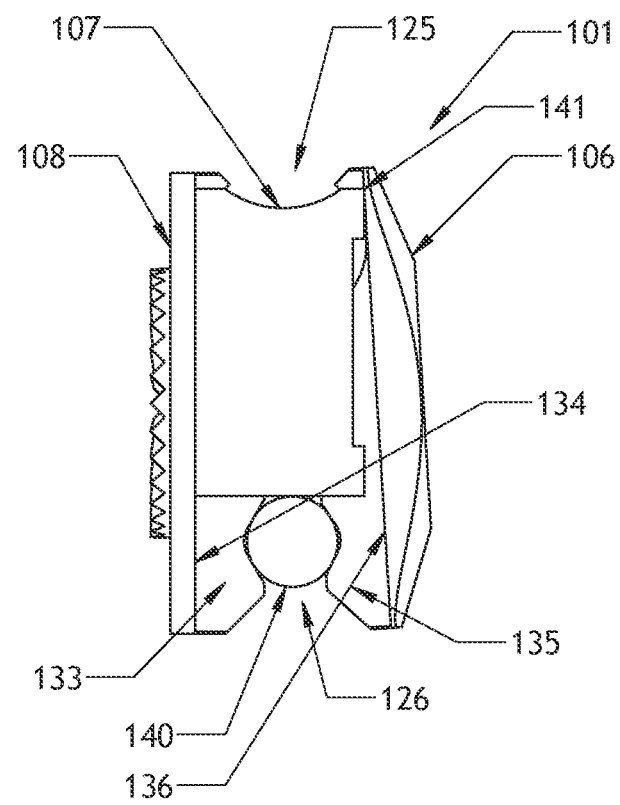
FIG. 9 shows the jaw set holding an element of a second size in the second passage according to one or more aspects of the present disclosure.

FIG. 9 shows the jaw set 101 in a second position where the sliding spacer 107 and at least one of the inner and outer jaws 108, 106 are in contact at a second point away from the fixation element and away from the fastener or threaded shaft 103. Here, a fixation element 140 may be located in the second passage 126 of the jaw set 101. In this embodiment, the element 140 may be a fixation pin, having a size or diameter less than a size or diameter of a fixation bar. In an exemplary embodiment, the spacer 107 is moved to the other end of the jaw set, and the outer jaw 106 is in contact with the spacer 107 at contact points that correspond to the reference numbers 141 in FIG. 9 on the other outer edges 141, 141a of the spacer, furthest from the second element 140. The contact point that corresponds to the reference numbers 141 in FIG. 9 may act as a fulcrum for the outer jaw to pivot or rotate to increase or decrease the width of the passage 126. Although shown as a contact point with the outer jaw 106, other embodiments utilize a contact point or contact fulcrum with the inner jaw, while yet other embodiments utilize contact points or contact fulcrums on both the inner and outer jaws 108, 106 at the same time. Also, in the configuration shown in FIG. 9, the spacer 107 is located so no element can be introduced into the first passage 125. It may do this because the sliding spacer 107 intersects with the first passage 125 and mechanically interferes or blocks introduction of an element into the first passage 125.

The spacer 107 in FIG. 9 operates differently than known latches like that described in U.S. Pat. No. 9,138,260. The known latch is provided to provisionally lock the outer and inner jaw to resist them from opening and allowing the fixation element to be removed. The known latch slides into alternative positions depending upon the size of the fixation element being gripped, but the fixation element is always gripped by the first end of the jaw set, and the latch always contacts the second end of the jaw set. In contrast, the sliding spacer 107 described herein is configured to contact the second end of the jaw set when the first end holds a fixation element, and to contact the first end when the second end holds a fixation element. As can be seen in FIGS. 8 and 9, the outer jaw 106 is configured to tilt relative to the inner jaw 108 to allow the fixation elements 130, 140 to enter between the outer and inner jaws 106, 108.

Figure 10:
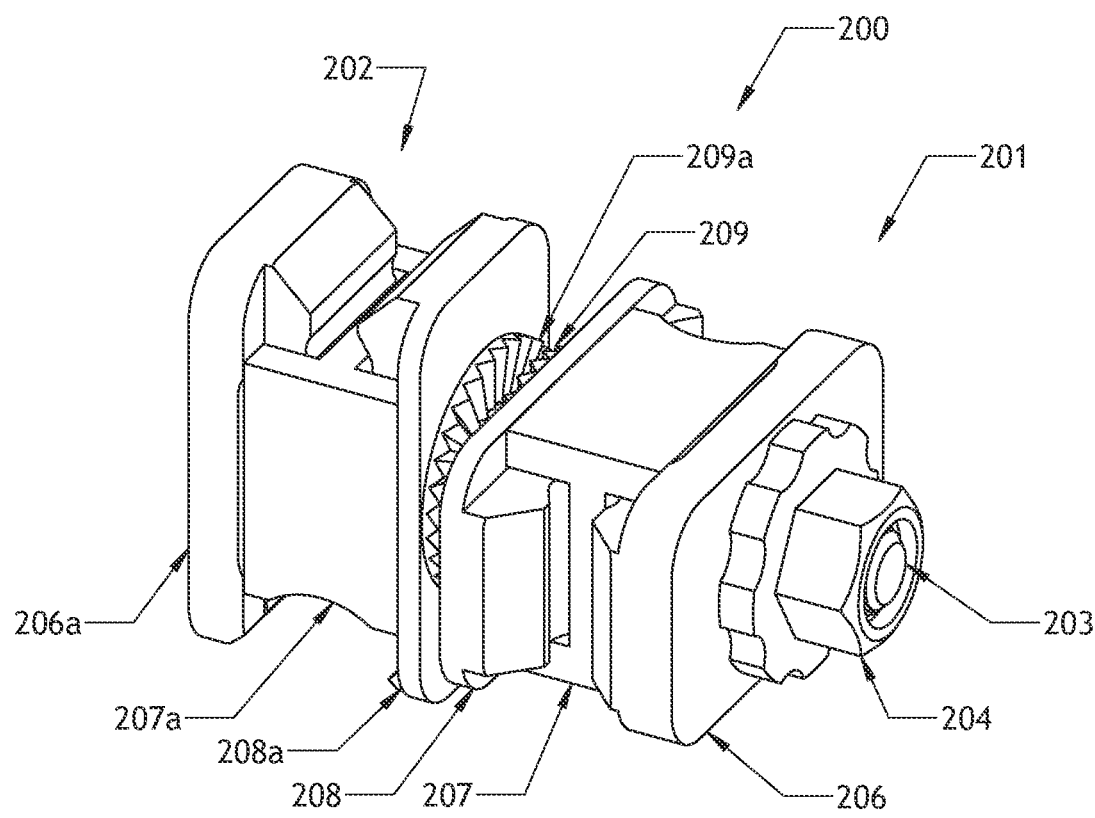
FIG. 10 shows a perspective view of a clamp made with a second embodiment jaw set where the jaws slide relative to each other according to one or more aspects of the present disclosure.

FIG. 10 is a perspective view of an external fixation clamp assembly 200 made with an alternative embodiment jaw set 201 according to one or more aspects of the present disclosure. Some features are similar to or the same as described with reference to the other embodiments, and will not be re-described here. This clamp may incorporate a second similar jaw set 202, but other jaw sets or other external fixation devices could be mated to the first jaw set as described above with reference to the clamp assembly 100. To apply clamping force to the jaw set, a threaded shaft 203 and nut 204 act on the other jaw set 202 or an alternative fixation device in place of the jaw set 202. In some embodiments, the outer jaw 206 rests against the spacer 207 which rests against the inner jaw 208. The second device in FIG. 10 is also an alternative embodiment jaw set, so there is a similar outer jaw 206a, spacer 207a, and inner jaw 208a. The inner jaw may have rotation resisting serrations 209 which seat into similar serrations 209a on the other device 202, although other rotation resisting features are contemplated, including relying solely on the force of friction.

Figure 11:
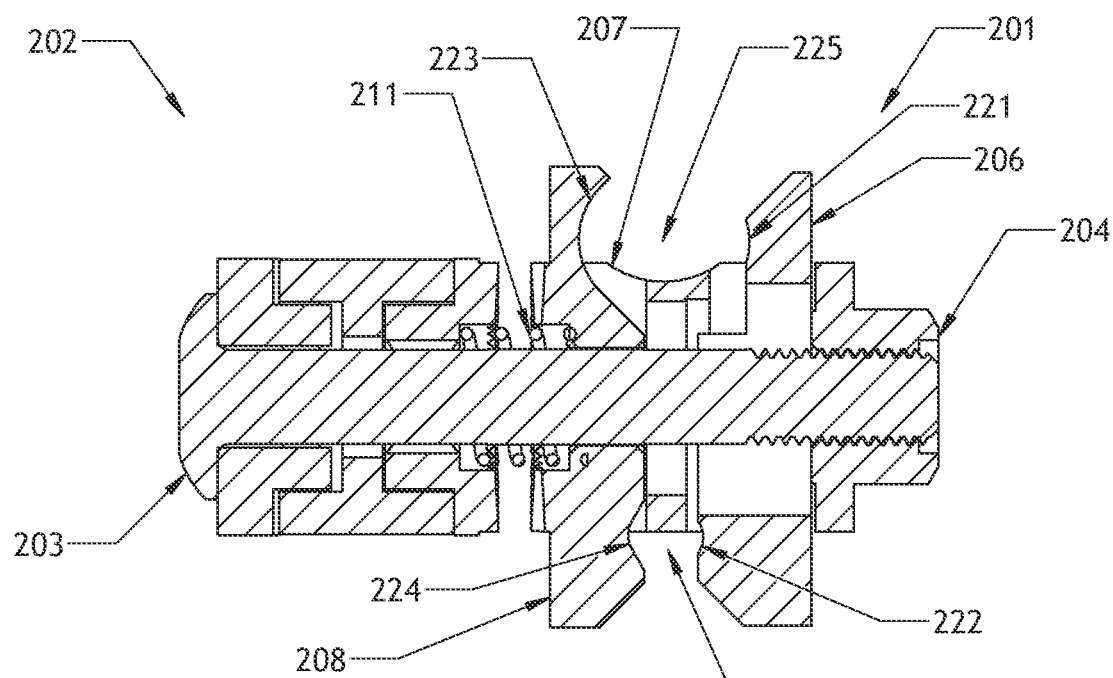
FIG. 11 shows a section view of the second embodiment jaw set according to one or more aspects of the present disclosure.

FIG. 11 is a section view of the device through the axis of the shaft and perpendicular to the axis of any fixation element according to one or more aspects of the present disclosure. Visible in this view is a biasing member shown as a spring 211 which may bias or selectively hold the jaw sets apart. The spring is a biasing feature that makes the clamp easier to snap onto the fixation element and remain in place prior to tightening, but the spring may not be required for the device to function. Other biasing elements are contemplated to be added to this device, including biasing elements that return the spacer 207 or the outer jaw 206 to the middle position relative to the inner jaw 208. FIG. 11 shows how tightening the nut 204 can compress the jaw sets 201, 202 against the head of the shaft 203. FIG. 11 shows that, in some embodiments, the outer jaw 206 may have a first groove 221 and a second groove 222. Similarly, the inner jaw 208 may have a third groove 223 and a fourth groove 224. When the jaw set 201 is assembled, the first and third groove 221, 223 may combine to form a first passage 225 to grip a fixation element, and the second and fourth groove 222, 224 may combine to form a second passage 226 to grip a differently sized fixation element.

Figure 12:
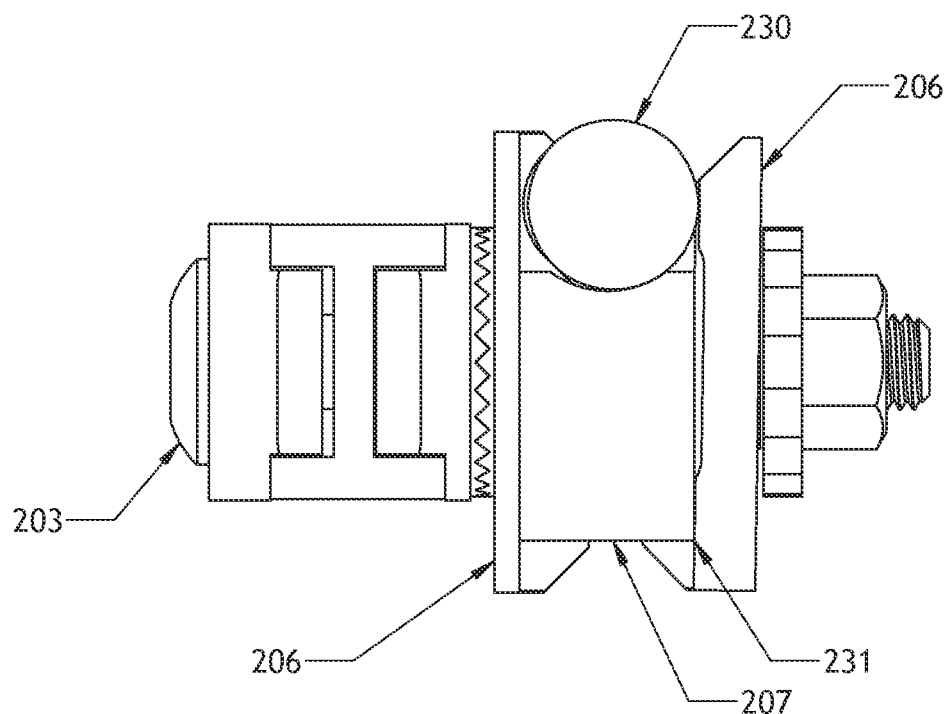
FIG. 12 shows the second embodiment jaw set gripping a first element in the first passage according to one or more aspects of the present disclosure.

FIG. 12 shows a fixation element 230 located in the first passage 225 of the jaw set according to one or more aspects of the present disclosure. In an exemplary embodiment, to insert the fixation element 230 into the passage 225, the outer jaw 206 and spacer 207 are moved transversely relative to the inner jaw 208 and shaft 203. In a further exemplary embodiment, to hold the fixation element 230 in the passage 225, the outer jaw 206 is moved back in the position to form the passage 225. It is contemplated that in various embodiments a biasing element can be used to return the outer jaw 206 into position, but the embodiment as shown in FIG. 12 (which is a non-limiting embodiment) is configured to have that step performed by the user. In an exemplary embodiment, the spacer 207 remains in a position away from the first passage, and the outer jaw 206 is in contact with the spacer 207 on the outer edge 231 of the spacer 207 furthest from the element 230. Because the spacer is displaced away from the element, the edge in contact is located away from the shaft 203. In the configuration shown in FIG. 12, the spacer is also preventing introduction of an element into the second passage.

Figure 13:
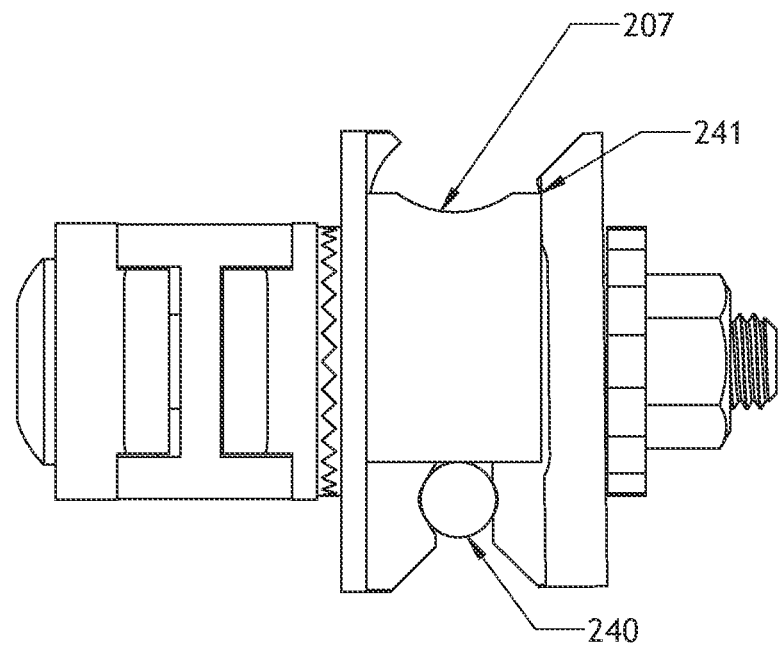
FIG. 13 shows the second embodiment jaw set gripping a second element of a different size than the first element in the second passage according to one or more aspects of the present disclosure.

FIG. 13 shows a second fixation element 240 located in the second passage 226 of the jaw set 201 according to one or more aspects of the present disclosure. In an exemplary embodiment, to introduce the element 240 into the passage 226, the outer jaw 206 and spacer 207 are moved transversely relative to the inner jaw 208 and shaft 203. In a further exemplary embodiment, to hold the fixation element 240 in the passage 226, the outer jaw 206 is moved back in the position to form the passage 226. The spacer 207 remains in a position away from the second passage. In some embodiments, the outer jaw 206 is in contact with the spacer 207 on the other outer edge 241 of the spacer 207, furthest from the second element. Also, in the configuration shown in FIG. 13, the spacer 207 is located so no element can be introduced into the first passage.

Figure 14:
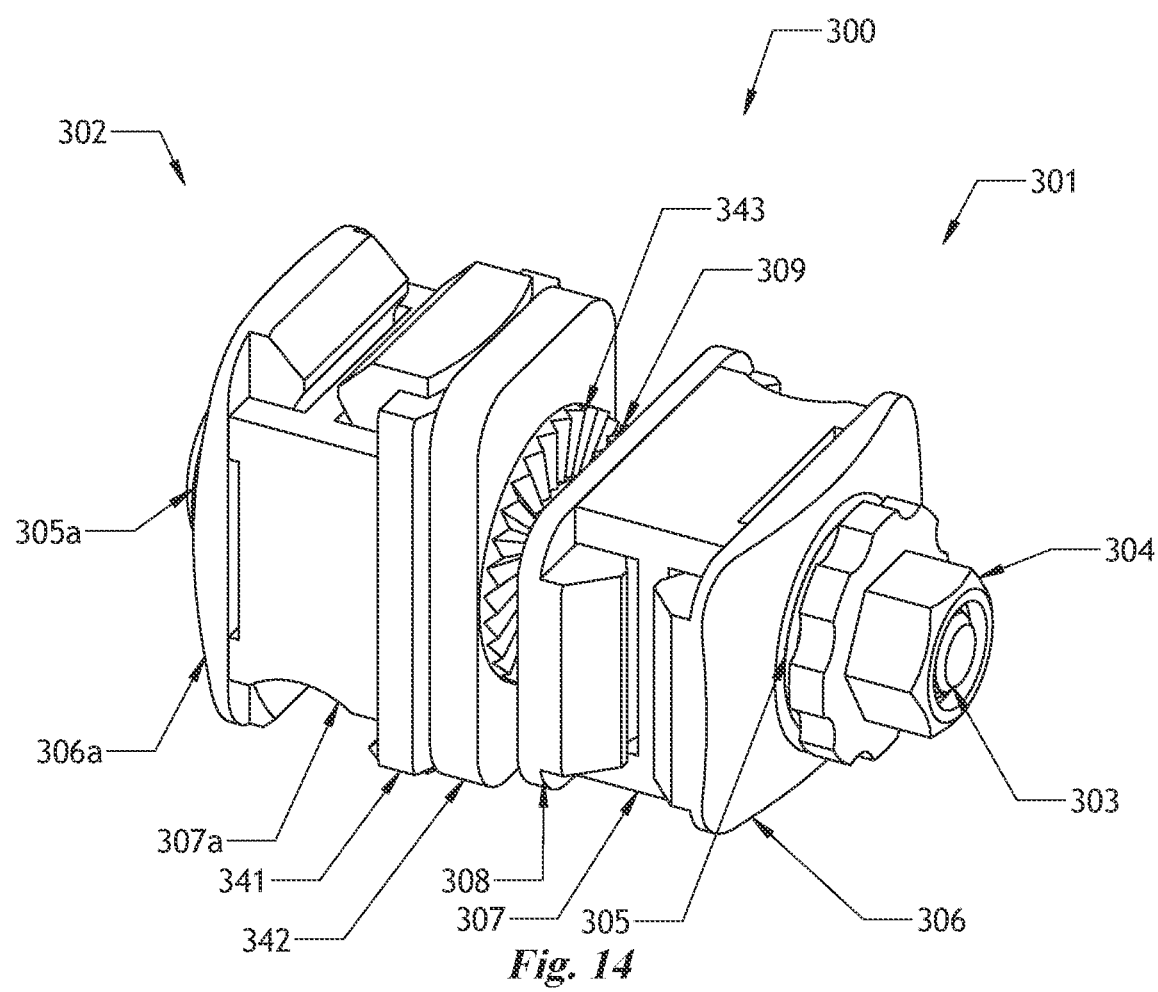
FIG. 14 shows a clamp made from a third embodiment jaw set where the jaw set is configured to tilt relative to the shaft according to one or more aspects of the present disclosure.

FIG. 14 shows an alternative embodiment according to one or more aspects of the present disclosure. Some features are similar to or the same as described with reference to the other embodiments, and will not be re-described here. In some embodiments, a clamp 300 may be made from a jaw set 301 and a jaw set 302. Jaw set 301 may include an outer jaw 306, a spacer 307, and an inner jaw 308 and may be configured similar to the example embodiments discussed above, including the jaw set 101. The alternative embodiment jaw set 302, may be made from a similar outer jaw 306a and spacer 307a, but the inner jaw 341, is, in some embodiments, configured to mate with a saddle 342. The saddle 342 may incorporate serrations 343 that mate with the serrations 309 on the inner jaw 308. To clamp the two jaw sets 301, 302 together, there is a threaded shaft 303 and a nut 304. Optional washers 305, 305a are shown in this embodiment. In some implementations, the saddle may be referred to as a coupling mechanism arranged to couple the two jaw sets 301, 302 together.

Figure 15:
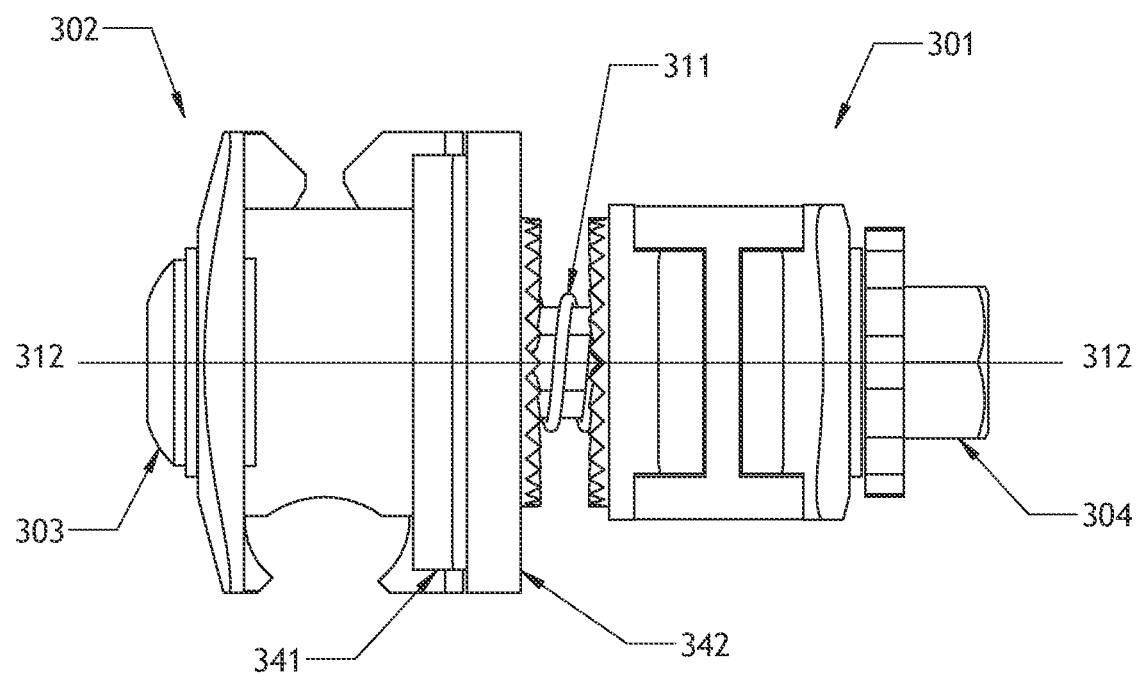
FIG. 15 shows the clamp with the third embodiment jaw set as seen from the side according to one or more aspects of the present disclosure.

In FIG. 15, a side view of the clamp is shown according to one or more aspects of the present disclosure. A line 312-312 is shown substantially down the center of the clamp. Visible in this view is a biasing element shown as a spring 311, which in some embodiments may maintain or selectively hold the jaw sets apart.

Figure 16:
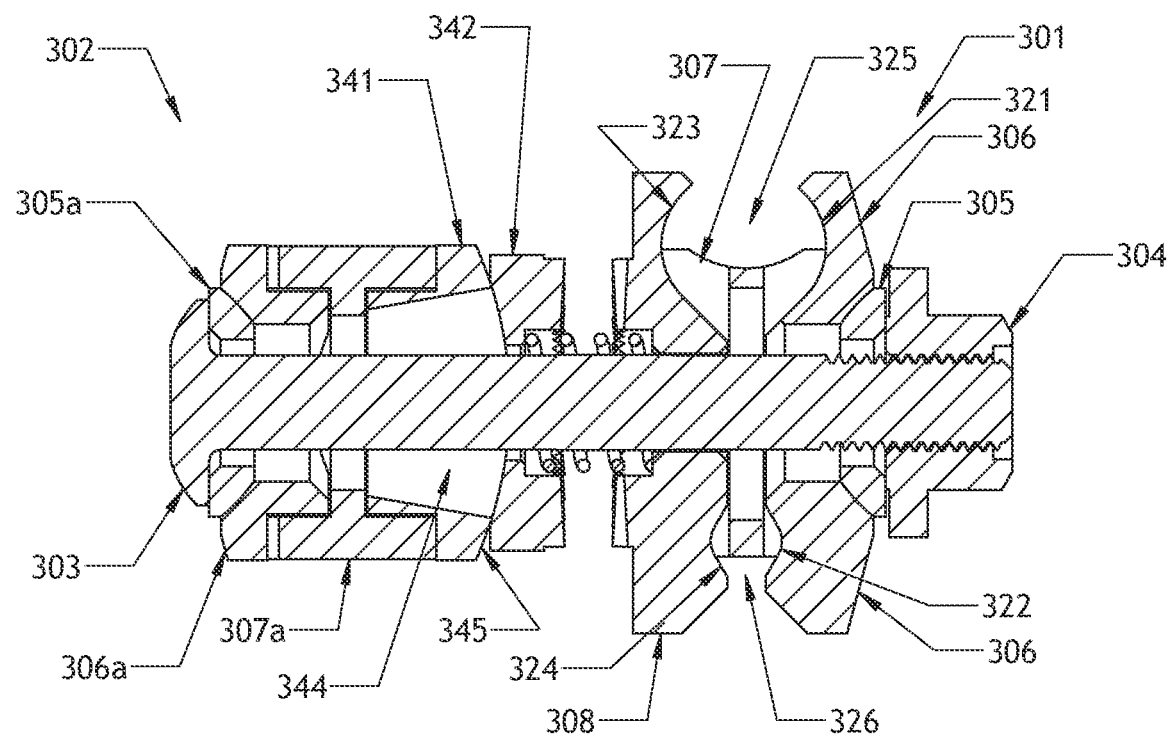
FIG. 16 shows a section view taken through line 312-312 in FIG. 15 showing the interface between the inner jaw and the saddle according to one or more aspects of the present disclosure.

FIG. 16 is the section view of the clamp taken through the line 312-312 according to one or more aspects of the present disclosure. In some embodiments, the inner jaw 341 may have a convex lower surface 345 that fits against the saddle 342. An opening 344 in the inner jaw 341 may be configured such that the jaw set can be tilted relative to the shaft. The saddle 342 may include a relatively planar surface on a first side and include a partially cylindrical depression or concavity on the opposing side. This may enable the jaw set 302 to pivot or tilt as discussed above. The opening 344 may be formed with a wider opening facing toward the opposing jaw set 301, and a more narrow opening adjacent the spacer 307a and the outer jaw 306a. The saddle 342 may mate with the inner jaw in a manner that allows the inner jaw, the outer jaw, and the sliding spacer to roll about an angle transverse to both the axis of the fixation element carried by the inner jaw and the outer jaw and the axis of the fastener.

Figure 17:
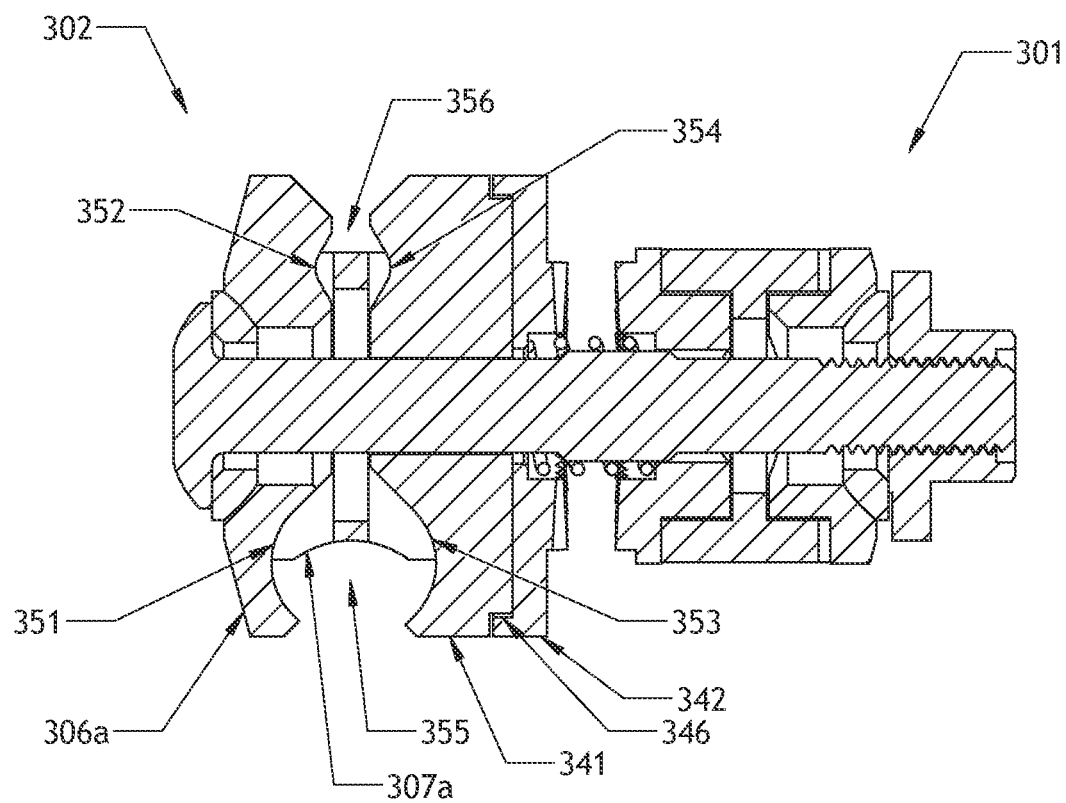
FIG. 17 shows a section view perpendicular to the view shown in FIG. 16 according to one or more aspects of the present disclosure.

FIG. 17 shows the same clamp in a section perpendicular to the view in FIG. 16 according to one or more aspects of the present disclosure. In FIG. 17, the inner jaw 341 is shown in section through the profile. In various embodiments, the saddle 342 may have a pocket with side walls 346 that maintain the relative rotation about the shaft between the inner jaw and the saddle while allowing the jaw set to tilt. The inner jaw also may have a first groove 353 and a second groove 354. The outer jaw 306a may have a first groove 351 and a second groove 352. Together, in an exemplary embodiment, the first grooves 351 and 353 form a first passage 355, and the second grooves 352 and 354 form a second passage 356.

In an exemplary embodiment, clamp 300 shows the embodiment jaw set 302 joined to another embodiment jaw set 301. It is contemplated that the jaw set 302 could be joined to another device, such as, for example, a multi-pin clamp or a telescoping tube, to form a different configuration external fixation frame.

Figure 18:
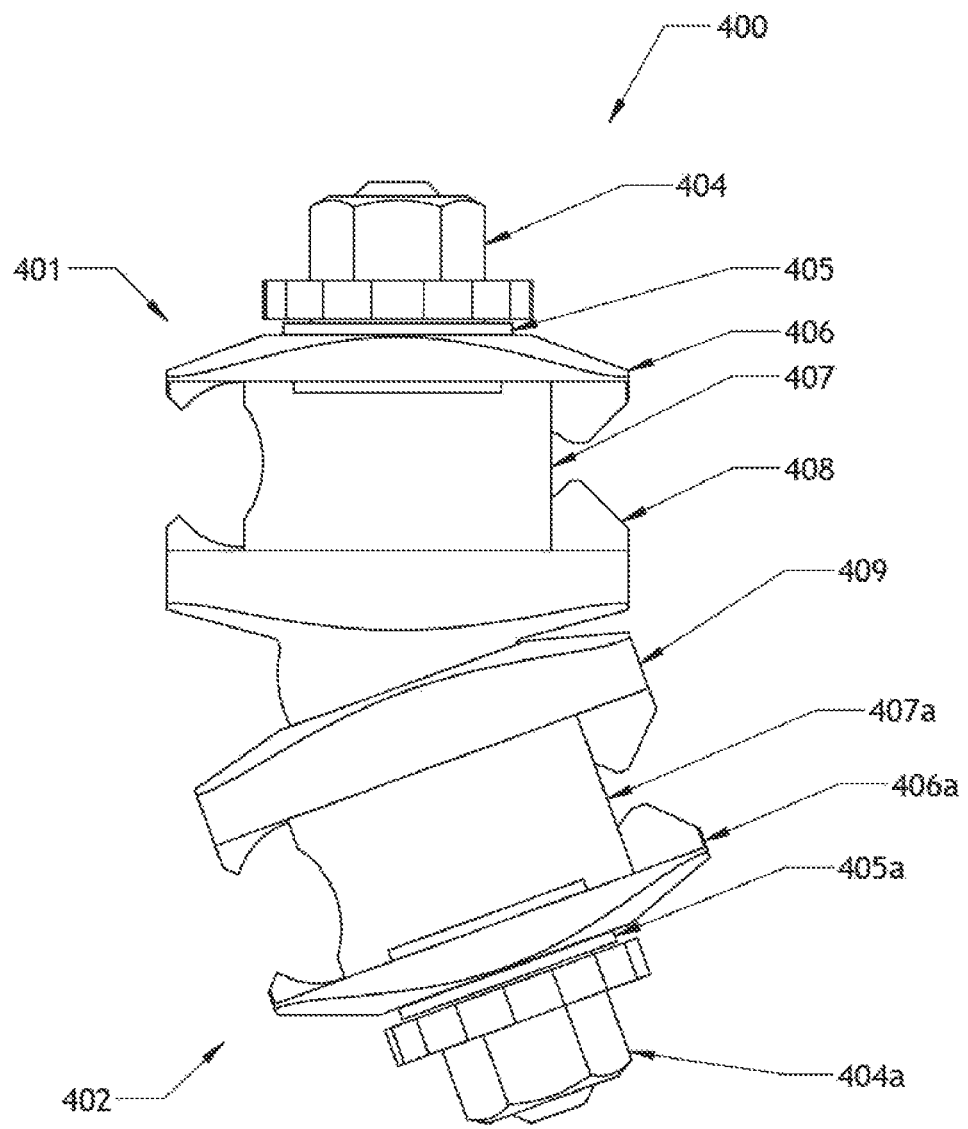
FIG. 18 shows a fourth embodiment of the invention where the inner jaw mates with another device via a ball joint according to one or more aspects of the present disclosure.

FIG. 18 shows another clamp 400 according to one or more aspects of the present disclosure. Some features are similar to or the same as described with reference to the other embodiments, and will not be re-described here. In some embodiments, clamp 400 is made from one embodiment jaw set 401 mated to another embodiment jaw set 402. Both jaw sets may have washers 405, 405a, outer jaws 406, 406a, and spacers 407, 407a. In an exemplary embodiment, the first inner jaw 408 and the second inner jaw 409 may mate together at a ball and socket joint.

Figure 19:
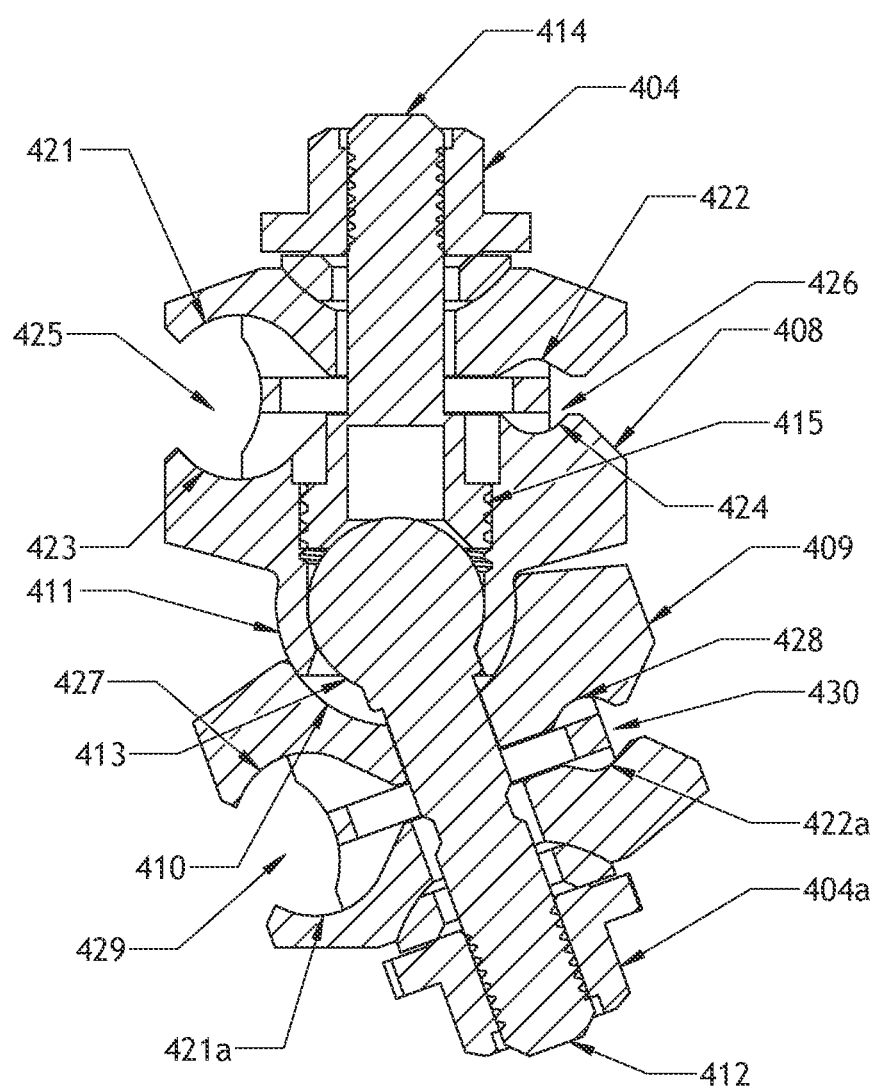
FIG. 19 shows the section view of the fourth embodiment, showing the inner jaw ball and inner jaw socket configuration according to one or more aspects of the present disclosure.

FIG. 19 shows a section view of the clamp 400 according to one or more aspects of the present disclosure. In various embodiments, the jaw set 401 may have a stud 414 that is threaded into the inner jaw 408. In an exemplary embodiment, when the nut 404 is tightened, the jaw set 401 is locked, but the ball joint may still be free to move if the other jaw set 402 is still unlocked. In some embodiments, inner jaw 409 may have a socket 410 which mates against a ball 411 on inner jaw 408. A threaded shaft 412 may have a ball 413 that rests in the ball 411 of the inner jaw 408. The shaft 412 goes through the inner jaw 409, spacer 407a and outer jaw 406a. In an exemplary embodiment, when the nut 404a is loose, the inner jaw 408 and the outer jaw are configured to pitch, roll, and yaw relative to a device comprising the ball 413. In an exemplary embodiment, when the nut 404a is tightened, the jaw set 402 locks and the ball joint locks as well.

FIG. 19 shows that the outer jaw 406 may have a first groove 421 and a second groove 422. Similarly, the inner jaw 408 may have a third groove 423 and a fourth groove 424. In some embodiments, when the jaw set 401 is assembled, the first and third groove 421, 423 may combine to form a first passage 425 to grip a fixation element, and the second and fourth groove 422, 424 may combine to form a second passage 426 to grip a differently sized fixation element. FIG. 19 shows a similar arrangement for the jaw set 402. The outer jaw 406a may have a first groove 421a and a second groove 422a. Similarly, the inner jaw 409 may have a third groove 427 and a fourth groove 428. In various embodiments, when the jaw set 402 is assembled, the first and third groove 421a, 427 may combine to form a first passage 429 to grip a fixation element, and the second and fourth groove 422a, 428 may combine to form a second passage 430 to grip a differently sized fixation element.

In an exemplary embodiment, the clamp 400 shows one embodiment jaw set 401 and another embodiment jaw set 402. It is contemplated to join jaw set 401 to a different device, such as, for example, a telescoping tube or a multi-pin clamp, as part of a different arrangement external fixation frame. It is also contemplated to join jaw set 402 to a different device as part of a different arrangement external fixation frame.

Figure 20:
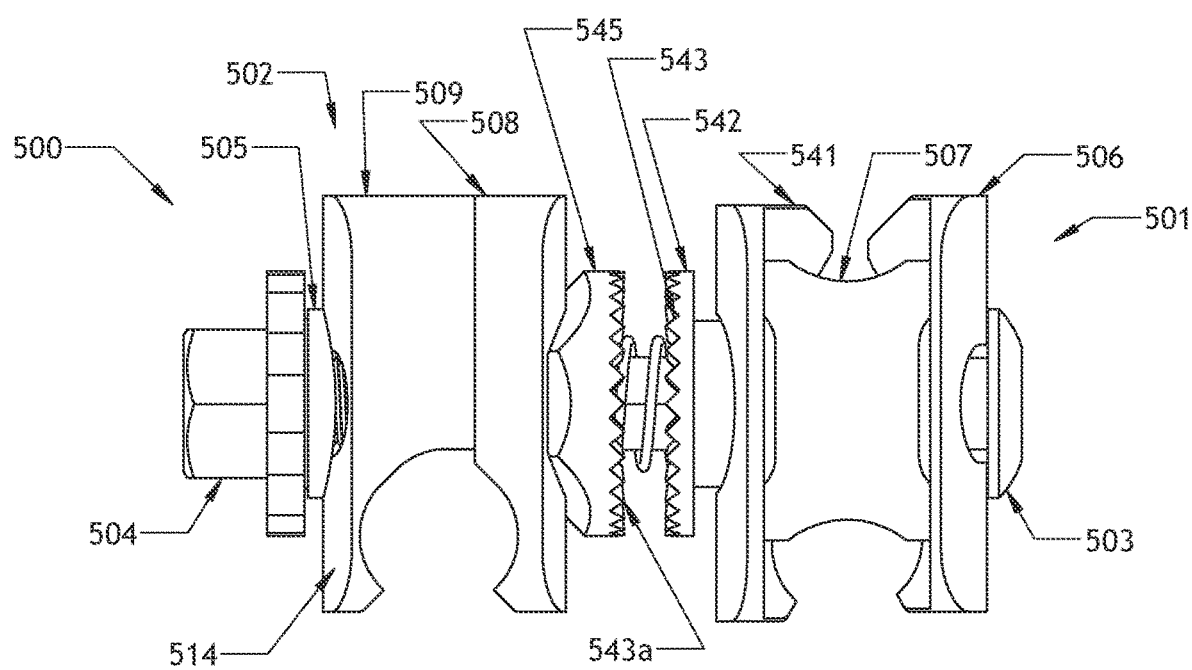
FIG. 20 shows a fifth embodiment of a clamp that incorporates a swivel element that allows the jaw set to tilt relative to the shaft according to one or more aspects of the current disclosure.

FIG. 20 shows another clamp 500 according to one or more aspects of the present disclosure. Some features are similar to or the same as described with reference to the other embodiments, and will not be re-described here. In some embodiments, clamp 500 is made from one embodiment jaw set 501 mated to another embodiment jaw set 502. The first jaw set 501 has an outer jaw 506, a spacer 507, and an inner jaw 541. The inner jaw 541 mates with a swivel 542. The second jaw set 502 has an outer jaw 509 and an inner jaw 508. The inner jaw 508 mates with a second swivel 545. In an exemplary embodiment, the first swivel 542 and the second swivel 545 mate together and the two jaw sets are clamped together by the fastener 503, the nut 504, and a washer 505. In some implementations, the first swivel 542 and the second swivel 545 may be referred to as a coupling mechanism arranged to couple the two jaw sets together. Other complete mechanisms are contemplated, including the other coupling mechanisms described herein.

Figure 21:
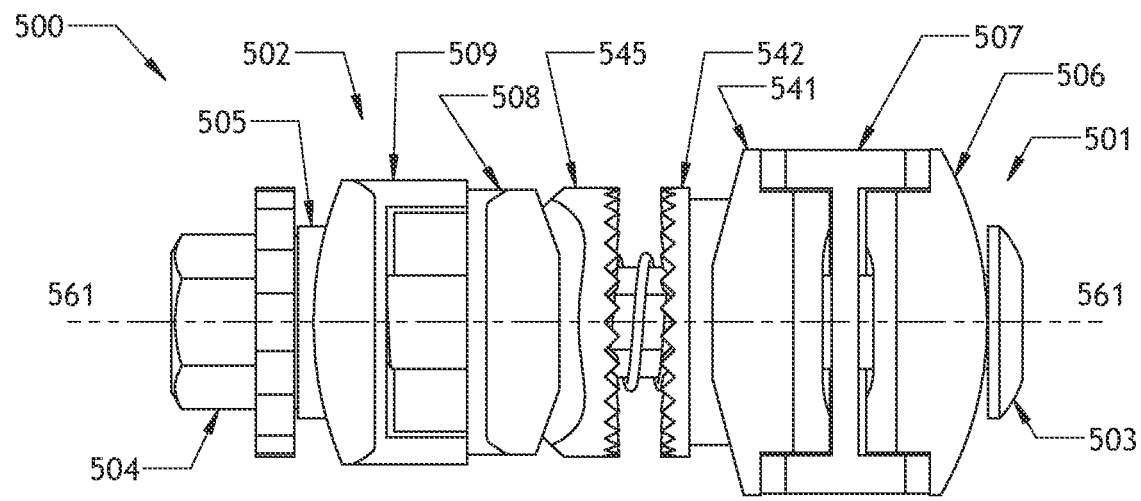
FIG. 21 shows the fifth embodiment clamp from a second perspective according to one or more aspects of the present disclosure.

FIG. 21 shows the same clamp as FIG. 20 from another perspective. In this figure, the jaw sets 501 502 are both in a neutral position. In this position, any fixation element inserted in either jaw set would be positioned perpendicular to the fastener 503.

Figure 22:
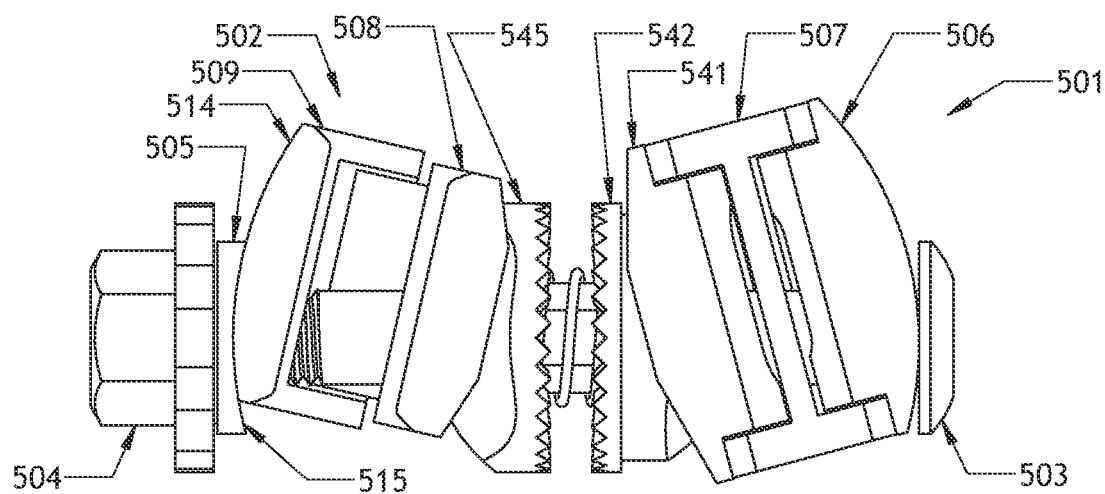
FIG. 22 shows the fifth embodiment clamp where the jaw set is tilted relative to the shaft according to one or more aspects of the present disclosure.

FIG. 22 shows the same clamp as FIG. 21 from the same perspective as FIG. 21. In this figure, the jaw sets 501 502 are shown in a swiveled position. This allows any fixation element inserted into either jaw set to be in a non-perpendicular position to the fastener 503.

Figure 23:
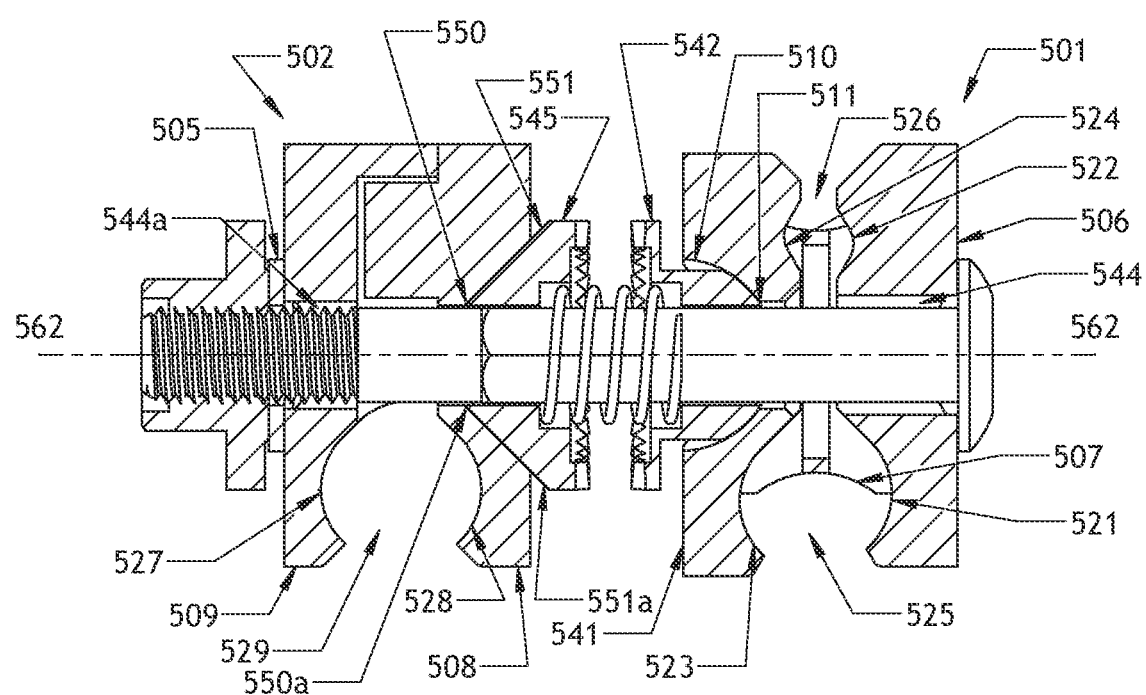
FIG. 23 shows a section view of the fifth embodiment clamp according to one or more aspects of the present disclosure.

FIG. 23 shows a section view of the clamp 500 according to one or more aspects of the present disclosure. The section view is taken through line 561 of FIG. 21. In FIG. 23 the outer jaw 506 has a first groove 521 and a second groove 522. Similarly, the inner jaw 541 may have a third groove 523 and a fourth groove 524. In some embodiments, when the jaw set 501 is assembled, the first and third groove 521, 523 may combine to form a first passage 525 to grip a fixation element, and the second and fourth groove 522, 524 may combine to form a second passage 526 to grip a differently sized fixation element. FIG. 23 also shows a similar arrangement for the jaw set 502. The outer jaw 509 may have a first groove 527. Similarly, the inner jaw 508 may have a third groove 528. In various embodiments, when the jaw set 502 is assembled, the first and third groove 527, 528 may combine to form a first passage 529 to grip a fixation element. The jaw sets 501 502 are configured to mate with swivels. In jaw set 501, the inner jaw 541 has an inner concave surface 510 which mates with the swivel outer convex surface 511. Similarly, in jaw set 502 the inner jaw 508 has an inner concave surface made from straight lines 550 550a which mates with the swivel outer convex surface 551 551a.

The inner concave surfaces of the inner jaws and the convex surfaces of the swivels are configured to allow the jaw sets to pivot about a transverse axis perpendicular to the longitudinal axis established by the clamping fastener and perpendicular to the axis of the fixation element. In this embodiment, the center of rotation of the jaw set is located on the swivel component side of the interface between the inner jaw and the swivel component. This is different than the articulation shown in clamp 300 or the known conventional clamp in U.S. Pat. No. 9,138,260, where the jaw set rotates on a saddle about an axis on the jaw set side of the saddle/inner jaw interface.

Figure 24:
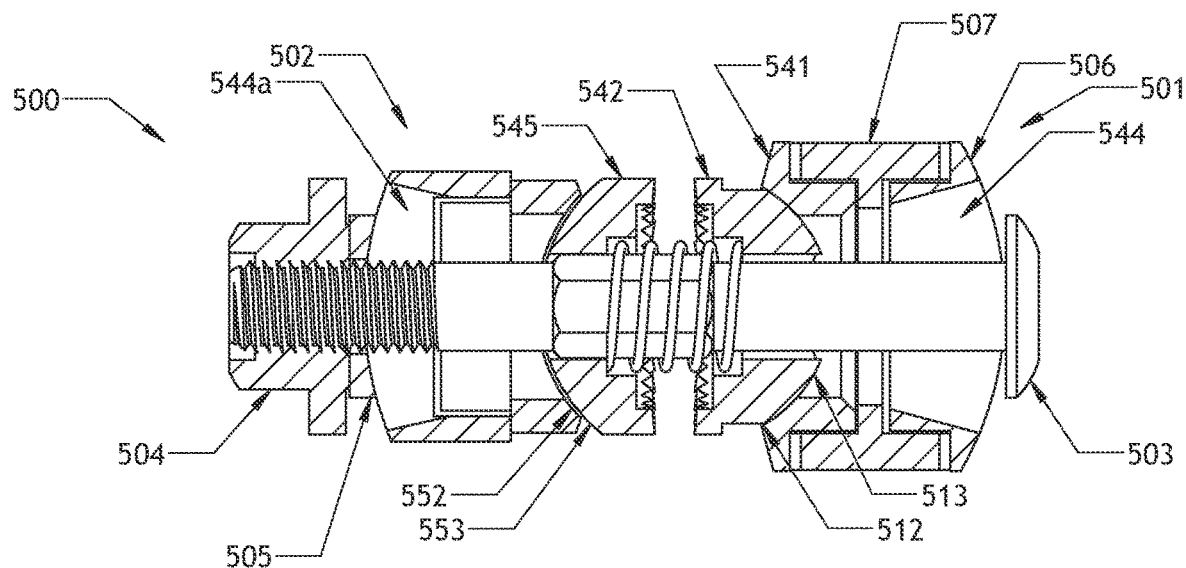
FIG. 24 shows a second section view of the fifth embodiment clamp according to one or more aspects of the present disclosure.

FIG. 24 is a section view of the clamp in FIG. 23 taken through the line 562. The jaw sets are shown in the same neutral orientation as FIG. 21. Swivel 542 may have a convex surface having a radius 513 which mates with the concave surface having a radius 512 of inner jaw 541. Convex radius 513 is a greater radius than convex radius 511. By having radius 511 swept along radius 513, the convex surface of swivel 542 is a torus. The concave radius 512 is a greater radius than concave radius 510. By having radius 510 swept along radius 512, the concave surface of inner jaw 541 is a torus. The inner jaw 541 mates and retains an orientation with the swivel 542 because the toroidal shapes are similar, aligning the axes of each torus. The two inner jaw radii 510 512 may also be the same, such that the inner jaw concave surface is a sphere. The two swivel radii 511 513 may also be the same, such that the swivel convex surface is a sphere. In some aspects, the surface is formed of cones, such as two cones.

In FIG. 24, inner jaw 508 shows inner concave surface 552, while swivel 545 shows outer surface 553. In the inner jaw 508, straight lines 550 550a are swept along a curve, creating a concave surface 552 with conical sides. On the swivel 545, straight lines 551 551a are swept along a curve, creating a convex surface 553 with conical sides. Inner jaw 508 mates against swivel 545 on the conical surfaces. The conical surfaces maintain alignment of the inner jaw to the swivel while allowing the jaw set to articulate about the swivel.

Figure 25:
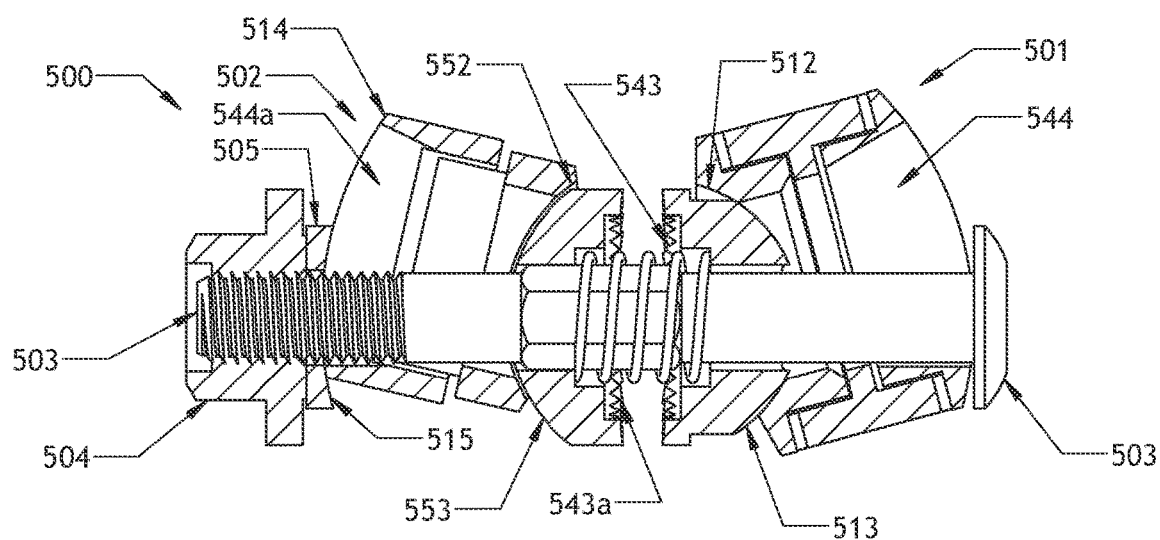
FIG. 25 shows a third section view of the fifth embodiment clamp where the jaw set is tilted relative to the shaft according to one or more aspects of the present disclosure.
Figure 26A:
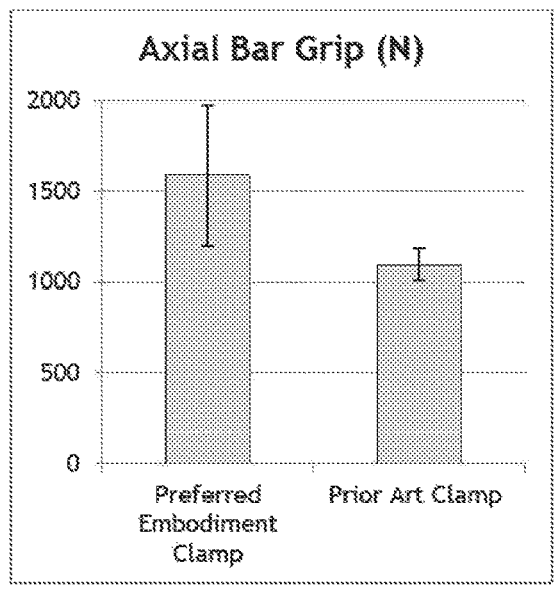
FIGS. 26a, 26b, 26c, and 26d are graphs showing grip forces of clamps according to the present disclosure compared to conventional clamps in FIGS. 1a and 1b.
Figure 26B:
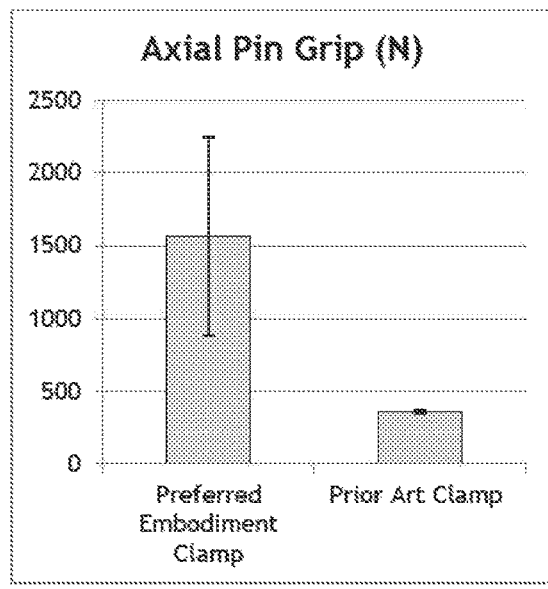
Figure 26C:
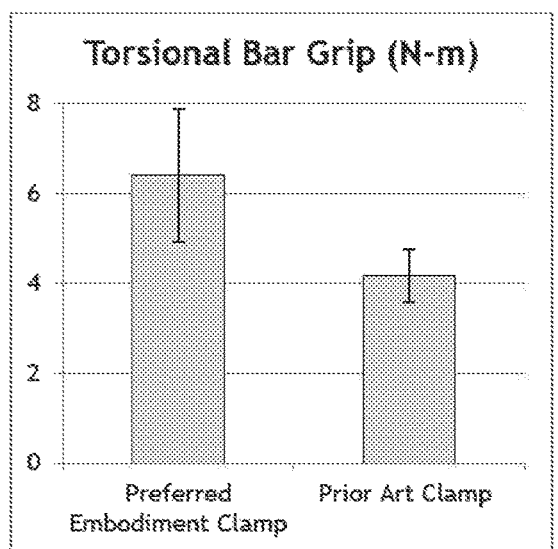
Figure 26D:
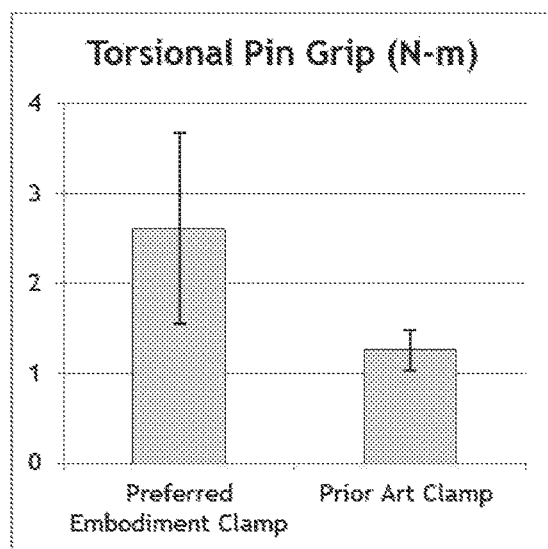

FIG. 25 shows a section view of the clamp 500 from the same orientation as in FIG. 24, but with the jaw sets 501 502 tilted relative to the fastener. The tilting of jaw set 501 is allowed to occur due to slot 544 being larger than the shaft. In this embodiment, the slot 544 is larger in the desired direction of tilt than it is in the perpendicular direction seen in FIG. 23. A similar slot 544a is incorporated into jaw set 502.

The nut 504 is tightened on the shaft 503, which brings the jaw sets 501 502 and the swivels 542 545 together. Serrations 543 543a on the swivel components 542 545 can be incorporated to increase the locking strength of the swivel to swivel interface over relying on pure friction. The jaw sets 501 502 are pinched between the swivels 542 545 and the washers 505 or the nut 504 and the head of the fastener 503, locking them in rotation as they are clamped onto fixation elements. In the embodiment shown, a single washer 505 is placed between the nut 504 and the outer jaw 509. The washer is intended to make for a smoother feel when tightening the nut, and to minimize marking on the outer jaw. The washer can be removed to reduce the number of components. The washer 505 could have a concave surface 515 on the side opposite the nut to increase the contact area with the outer surface 514 of outer jaw 509. A washer with a concave surface could be used between the head of the shaft 503 and the outer jaw 506 to increase the contact area. Increasing the contact area may provide a smoother unlocked articulation and a decrease in scratching between the components, but it is not required for high locking strength or general function of the articulating feature.

In an exemplary embodiment, the clamp 500 shows one embodiment jaw set 501 and another embodiment jaw set 502. It is contemplated to have an embodiment where jaw set 501 is joined to another jaw set 501. It is contemplated to join jaw set 501 to a different device, such as, for example, a telescoping tube or a multi-pin clamp, as part of a different arrangement external fixation frame. It is also contemplated to join jaw set 502 to a different device such as, for example, a jaw set 101, a telescoping tube or a multi-pin clamp, as part of a different arrangement external fixation frame.

The fixation clamps described herein may be sized and shaped to permit clamping on fixation elements of a variety of sizes. In some embodiments, a first end of the inner jaws and the outer jaws are sized and shaped to hold a fixation element of a diameter between 10 and 13 mm, and the second ends of the inner jaws and the outer jaws are configured to hold a fixation element of a diameter between 3 and 6.5 mm. In some implementations, the first ends of the jaws are configured to hold a fixation element of a diameter between 6 and 9 mm, and the second ends of the jaws are configured to hold a fixation element of a diameter between 3 and 5 mm. In yet other embodiments, the first ends of the jaws are configured to hold a fixation element of a diameter between 4 and 6 mm, and the second ends of the jaws are configured to hold a fixation element of a diameter between 2 and 4 mm. And in yet other embodiments, the first ends of the jaws are configured to hold a fixation element of a diameter of 11 mm, and the second ends of the jaws are configured to hold a fixation element of a diameter of 5 mm. These values are for example only, and other sizes are also contemplated.

Figure 1B:
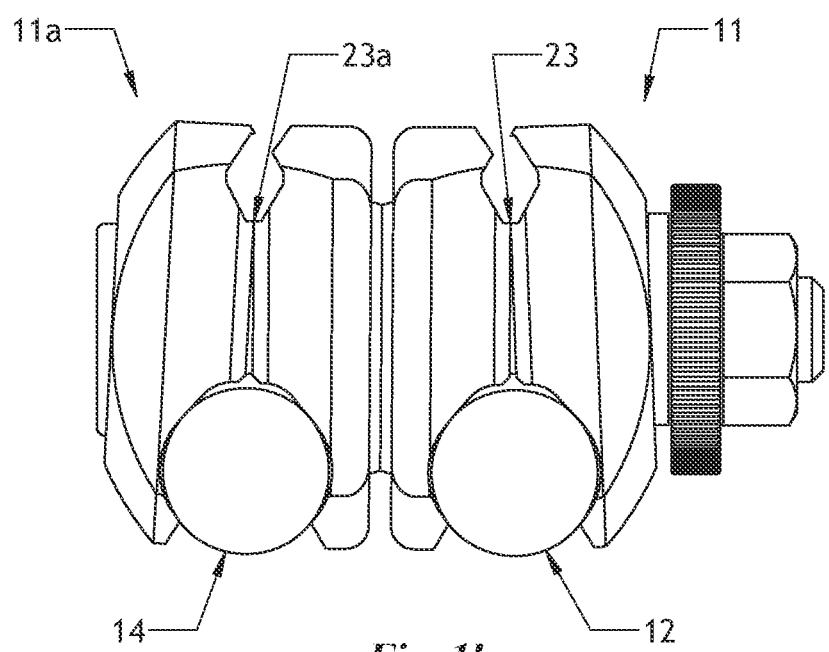
FIG. 1b shows a conventional device with jaw sets that have two passages where the first passage of both jaw sets is configured to hold an element of the first size.

To verify the performance improvement provided by the slider, grip strength testing of fixation elements was conducted. The testing compared prior art clamps according to FIGS. 1a and 1b with the clamps according to FIG. 3. Both the prior art clamps and the preferred embodiment clamps were made from titanium alloy. The grip strength of the clamps was compared when gripping 11 mm diameter carbon fiber bars, as well as when gripping 5 mm stainless steel pins. Axial grip tested the strength of the clamp in holding the bar or pin from slipping along its longitudinal direction. Torsion grip tested the resistance of the clamp from allowing the cylindrical element to rotate. The clamps were all tightened to the same 10 N-m torque. FIG. 26 shows the relative results of the different tests. The difference in grip strength is significant for all tests, with a big difference shown on the pin grip.

In all the previous descriptions, the elements have been shown as cylinders. Other external fixation elements, such as rings, square bars, rectangular bars, and hexagonal bars may all be used as frame components. It is contemplated that the jaw sets can be configured to grip any of these shapes and other frame component shapes of the like.

Persons of ordinary skill in the art will appreciate that the embodiments encompassed by the present disclosure are not limited to the particular exemplary embodiments described above. In that regard, although illustrative embodiments have been shown and described, a wide range of modification, change, and substitution is contemplated in the foregoing disclosure. It is understood that such variations may be made to the foregoing without departing from the scope of the present disclosure. Accordingly, it is appropriate that the appended claims be construed broadly and, in a manner, consistent with the present disclosure.

What is claimed is:

1. An external fixation clamp jaw set configured to grip at least one fixation element, comprising:
   an outer jaw with a first end and a second end;
   an inner jaw with a first end and a second end, the first end of the inner jaw and the first end of the outer jaw being disposed to cooperatively form a first passage sized to grip a first fixation element of the at least one fixation element, the first fixation element having a first size, the inner jaw having a concave surface opposite the outer jaw, the second end of the inner jaw and the second end of the outer jaw are disposed to cooperatively form a second passage sized to grip a second fixation element of the at least one fixation element, the second fixation element having a second size;
   a fastener configured to clamp the inner jaw and the outer jaw to the first or the second fixation element, the fastener having a fastener axis, and
   a swivel component with a convex surface shaped to mate to the concave surface of the inner jaw;
   wherein the inner jaw is configured to mate with the swivel component and allow the inner jaw and the outer jaw to roll about an axis transverse to both an axis of the at least one fixation element and the axis of the fastener; and
   wherein the external fixation clamp jaw set further includes a sliding spacer slidably associated with the inner jaw and the outer jaw to slide in a direction transverse to the fastener axis, the sliding spacer being structurally associated with the inner jaw and the outer jaw so that when the first size fixation element is introduced into the first passage, the sliding spacer moves to a first position where the sliding spacer and at least one of the inner and the outer jaws are in contact at a first location away from the fastener, and alternately when the second size fixation element is introduced into the second passage, the sliding spacer moves to a second position where the sliding spacer and at least one of the inner and the outer jaws are in contact at a second location away from the fastener.

2. The jaw set of claim 1, wherein the swivel component is configured to lock the first and the second jaws at a tilt relative to the fastener at the same time the fastener clamps the inner jaw and the outer jaw to the at least one-fixation element.

3. The jaw set of claim 1, wherein the convex surface of the swivel component is a toroidal shape.

4. The jaw set of claim 1, wherein the convex surface of the swivel component is a cylindrical shape.

5. The jaw set of claim 1, wherein the convex surface of the swivel component is a shape comprising two cones.

6. The jaw set of claim 1, wherein the convex surface of the swivel component is a partial sphere.

7. The jaw set of claim 1, wherein the swivel component has a serrated surface opposite the convex surface.

8. The jaw set of claim 1, wherein the outer jaw has a convex surface.

9. The jaw set of claim 8, wherein the convex surface of the outer jaw mates with a flat surface of the fastener.

10. The jaw set of claim 8, wherein the convex surface of the outer jaw mates with a washer interposed between the outer jaw and the fastener.

11. The jaw set of claim 10, wherein the washer incorporates a convex surface to contact the outer jaw.

12. An external fixation clamp comprising:
a jaw set including an outer jaw and an inner jaw forming a first passage therebetween and a second passage therebetween, the jaw set being configured to capture a first rigid fixation element within the first passage having a first size and a second rigid fixation element within the second passage having a second size, the first size being different than the second size, the inner jaw having a concave cavity on a surface facing away from the outer jaw;
a clamping mechanism arranged to maintain an axial alignment of the outer jaw and the inner jaw;
a reference component offset along a longitudinal axis from the jaw pair;
a coupling mechanism arranged between the jaw set and the reference component, the coupling mechanism allowing the jaw set to rotate relative to the reference component about the longitudinal axis, the coupling mechanism comprising a convex surface interfacing with the concave cavity on the surface of the inner jaw facing away from the outer jaw, and the jaw set being pivotable on the coupling mechanism about a transverse axis that is perpendicular to the longitudinal axis;
wherein the jaw set further includes a sliding spacer cooperatively associated with the inner jaw and the outer jaw and arranged to slide in a direction transverse to an axis of the clamping mechanism, the sliding spacer being structurally associated with the outer and inner jaws so that when the first rigid fixation element having the first size is introduced into a corresponding first end, the sliding spacer moves to a first position where the sliding spacer and at least one of the inner and outer jaws are in contact at a first location away from the clamping mechanism, and alternately when the second rigid fixation element having the second size is introduced into the second passage, the sliding spacer moves to a second position where the sliding spacer and at least one of the inner and outer jaws are in contact at a second location away from the clamping mechanism.

13. The external fixation clamp of claim 12, wherein the clamping mechanism is a nut combined with a threaded stud.

14. The external fixation clamp of claim 13, wherein the nut comprises a flat surface that articulates against a curved outer surface of the outer jaw, the nut being rotatable to lock articulation of the jaw set when tightened on the stud.

15. The external fixation clamp of claim 14, comprising a washer between the nut and the curved outer surface of the outer jaw.

16. The external fixation clamp of claim 15, wherein the washer comprises a curved surface that fits against the curved outer surface of the outer jaw.

17. An external fixation clamp comprising:
a first jaw set including an outer jaw and an inner jaw forming a first passage therebetween, the first jaw set being configured to capture a first fixation element within the first passage;
a second jaw set offset along a longitudinal axis from the first jaw set, the second jaw set configured to hold a fixation element, the second jaw set comprising: an inner jaw with a first end shaped to engage a first size fixation element and a second end shaped to engage a second size fixation element, and an outer jaw with a first end shaped to engage the first size fixation element and a second end shaped to engage the second size fixation element; and
a fastener passing through the first and second jaw sets, the fastener configured to clamp the jaws of at least the second jaw set to at least one of the first and the second fixation elements, the fastener having an axis,
wherein at least the second jaw set further includes a sliding spacer interposed between the inner and outer jaws of the second jaw set arranged to slide in a direction transverse to the axis of the fastener, the sliding spacer being structurally associated with the inner and outer jaws of the second jaw set so that when the first size fixation element is introduced into a corresponding first end of the second jaw set, the sliding spacer moves to a first position where the sliding spacer and at least one of the inner and outer jaws of the second jaw set are in contact at a first point away from the fastener, and alternately when the second size fixation element size is introduced into the second end of the second jaw set, the sliding spacer moves to a second position where the sliding spacer and at least one of the inner and outer jaws of the second jaw set are in contact at a second point away from the fastener.

18. The external fixation clamp of claim 17, wherein the external fixation clamp further includes a coupling mechanism arranged between the first and second jaw sets, the coupling mechanism allowing the first jaw set to rotate relative to the second jaw set about the longitudinal axis, the coupling mechanism comprising a convex surface interfacing with a concave cavity on a surface of the inner jaw of at least one of the first and second jaw sets, the inner jaw facing away from the outer jaw, at least one of the first and second jaw sets being pivotable on the coupling mechanism about a transverse axis that is perpendicular to the longitudinal axis; wherein the clamping mechanism locks both fixation elements and a position of the first jaw set relative to the second jaw set when applying clamping force.

* * * * *